(12) United States Patent
Park et al.

(10) Patent No.: US 10,376,424 B2
(45) Date of Patent: Aug. 13, 2019

(54) ABSORBENT ARTICLE WITH FLAT-BACK PROTECTION FEATURE

(71) Applicant: Kimberly-Clark Worldwide, Inc., Neenah, WI (US)

(72) Inventors: SoHyun S. Park, Neenah, WI (US); JaeEun Park, Yongin-Si (KR)

(73) Assignee: Kimberly-Clark Worldwide, Inc., Neenah, WI (US)

(*) Notice: Subject to any disclaimer, the term of this patent is extended or adjusted under 35 U.S.C. 154(b) by 3 days.

(21) Appl. No.: 15/550,369

(22) PCT Filed: Feb. 27, 2017

(86) PCT No.: PCT/US2017/019718
§ 371 (c)(1),
(2) Date: Aug. 10, 2017

(87) PCT Pub. No.: WO2017/151513
PCT Pub. Date: Sep. 8, 2017

(65) Prior Publication Data
US 2018/0098892 A1    Apr. 12, 2018

Related U.S. Application Data

(60) Provisional application No. 62/301,338, filed on Feb. 29, 2016.

(51) Int. Cl.
*A61F 13/472* (2006.01)
*A61F 13/511* (2006.01)
(Continued)

(52) U.S. Cl.
CPC .......... *A61F 13/472* (2013.01); *A61F 13/475* (2013.01); *A61F 13/4758* (2013.01);
(Continued)

(58) Field of Classification Search
CPC .. A61F 13/472; A61F 13/475; A61F 13/4758; A61F 13/511; A61F 13/51104; A61F 13/514
See application file for complete search history.

(56) References Cited

U.S. PATENT DOCUMENTS 2,408,508 A    10/1946  Canavan
3,092,109 A     6/1963  Mosier
(Continued)

FOREIGN PATENT DOCUMENTS

DE     8414734 U1    7/1987
DE    20302153 U1    7/2003
(Continued)

*Primary Examiner* — Tatyana Zalukaeva
*Assistant Examiner* — Gabriella E Burnette
(74) *Attorney, Agent, or Firm* — Kimberly-Clark Worldwide, Inc.

(57) ABSTRACT

An absorbent article includes a base-structure and an elevatable structure known as a flat-back protection feature, that is capable of rising above the base-structure during article use. The flat-back protection feature utilizes either differences in material length compared with the length of the adjacent base-structure, or elastic materials, to maintain the feature elevation above the base-structure, while the article is in an extended condition. The flat-back protection feature extends into the intergluteal cleft of a wearer during use. Embossment features on the absorbent article are used to facilitate folding of the absorbent article, enhance the functionality of the protection feature, and/or improve the ease of manufacture.

15 Claims, 14 Drawing Sheets

(51) Int. Cl.
*A61F 13/514* (2006.01)
*A61F 13/475* (2006.01)
(52) U.S. Cl.
CPC ......... *A61F 13/511* (2013.01); *A61F 13/514* (2013.01); *A61F 13/51104* (2013.01)

(56) References Cited

U.S. PATENT DOCUMENTS

| | | | |
|---|---|---|---|
| 3,575,174 | A | 4/1971 | Mogor |
| 4,067,336 | A | 1/1978 | Johnson |
| 4,533,357 | A | 8/1985 | Hall |
| 4,631,062 | A | 12/1986 | Schultz et al. |
| 4,773,905 | A | 9/1988 | Molee et al. |
| 4,936,839 | A | 6/1990 | Molee et al. |
| 5,007,906 | A | 4/1991 | Osborn, III et al. |
| 5,009,653 | A | 4/1991 | Osborn, III |
| 5,171,302 | A | 12/1992 | Buell |
| 5,197,959 | A | 3/1993 | Buell |
| 5,300,055 | A | 4/1994 | Buell |
| 5,324,278 | A | 6/1994 | Visscher et al. |
| 5,514,104 | A | 5/1996 | Cole et al. |
| 5,593,400 | A * | 1/1997 | O'Leary ........... A61F 13/49009 604/385.27 |
| 5,624,421 | A | 4/1997 | Dabi et al. |
| 5,674,214 | A | 10/1997 | Visscher et al. |
| 5,733,274 | A | 3/1998 | Osborn, III |
| 5,827,261 | A | 10/1998 | Osborn, III et al. |
| 5,853,403 | A | 12/1998 | Tanzer et al. |
| 5,868,727 | A | 2/1999 | Barr et al. |
| 6,042,575 | A | 3/2000 | Osborn, III et al. |
| 6,156,951 | A | 12/2000 | Gustafsson et al. |
| 6,293,935 | B1 | 9/2001 | Kimura et al. |
| 6,296,628 | B1 | 10/2001 | Mizutani |
| D452,563 | S * | 12/2001 | Mok ............................ D24/124 |
| 6,352,529 | B1 | 3/2002 | Kreutz et al. |
| 6,395,956 | B1 | 5/2002 | Glasgow et al. |
| 6,410,822 | B1 | 6/2002 | Mizutani |
| 6,423,043 | B1 * | 7/2002 | Gustafsson ......... A61F 13/4702 604/378 |
| 6,447,495 | B1 | 9/2002 | Luizzi et al. |
| 6,448,466 | B1 | 9/2002 | Ribeiro De Carvalho |
| 6,471,682 | B2 * | 10/2002 | Kashiwagi ........ A61F 13/47263 604/378 |
| 6,475,199 | B1 | 11/2002 | Gann et al. |
| 6,475,203 | B1 | 11/2002 | Rubio |
| 6,613,031 | B2 | 9/2003 | Glasgow et al. |
| 6,620,144 | B1 | 9/2003 | Glasgow et al. |
| 6,632,210 | B1 | 10/2003 | Glasgow et al. |
| 6,652,498 | B1 | 11/2003 | Glasgow et al. |
| 6,676,649 | B2 | 1/2004 | Mizutani |
| 6,680,421 | B1 | 1/2004 | Ravo |
| 6,887,224 | B2 | 5/2005 | Rubio |
| 6,913,599 | B2 | 7/2005 | Mishima et al. |
| 6,929,629 | B2 | 8/2005 | Drevik et al. |
| 7,037,198 | B2 | 5/2006 | Hameen-Anttila |
| 7,037,297 | B2 | 5/2006 | Rubio |
| 7,056,311 | B2 | 6/2006 | Kinoshita et al. |
| 7,056,312 | B1 | 6/2006 | Metcalf |
| 7,156,832 | B2 | 1/2007 | Drevik et al. |
| 7,160,278 | B2 | 1/2007 | Mizutani et al. |
| 7,166,093 | B2 | 1/2007 | Drevik et al. |
| 7,312,372 | B2 | 12/2007 | Miyama et al. |
| 7,462,174 | B2 | 12/2008 | Nishitani et al. |
| 7,465,297 | B2 | 12/2008 | Watanabe et al. |
| 7,530,973 | B2 | 5/2009 | Tanio et al. |
| 7,549,981 | B2 | 6/2009 | Tanio et al. |
| 7,594,905 | B2 | 9/2009 | Tanio et al. |
| 7,597,690 | B2 | 10/2009 | Tanio et al. |
| 7,621,899 | B2 | 11/2009 | Fujikawa et al. |
| 7,648,490 | B2 | 1/2010 | Kuroda et al. |
| 7,708,725 | B2 | 5/2010 | Tamagawa et al. |
| 7,749,208 | B2 | 7/2010 | Moberg-Alehammar et al. |
| 7,763,001 | B2 | 7/2010 | Kawamura |
| 7,789,867 | B2 | 9/2010 | Carstens |
| 7,819,852 | B2 | 10/2010 | Feller et al. |
| 7,857,799 | B2 | 12/2010 | Lavash et al. |
| 7,875,013 | B2 | 1/2011 | Rubio |
| 7,976,525 | B2 | 7/2011 | McDaniel |
| 8,048,049 | B2 | 11/2011 | Fujikawa et al. |
| 8,093,449 | B2 | 1/2012 | Kudo et al. |
| 8,147,471 | B2 | 4/2012 | Roche Del Ayala et al. |
| 8,235,958 | B2 | 8/2012 | Kudo et al. |
| 8,246,593 | B2 | 8/2012 | Lavash |
| 8,251,966 | B2 | 8/2012 | Kudo et al. |
| 8,282,615 | B2 | 10/2012 | Een et al. |
| 8,343,124 | B2 | 1/2013 | Noda et al. |
| 8,377,022 | B2 | 2/2013 | Noda et al. |
| 8,419,699 | B2 | 4/2013 | Giloh |
| 8,439,886 | B2 | 5/2013 | Hashino et al. |
| 8,444,618 | B2 | 5/2013 | Kudo et al. |
| 8,500,709 | B2 | 8/2013 | Kudo et al. |
| 8,585,673 | B2 | 11/2013 | Noda et al. |
| 8,591,490 | B2 * | 11/2013 | Kudo .................. A61F 13/4704 604/385.01 |
| 8,771,250 | B2 | 7/2014 | Carbonari |
| 8,808,264 | B2 | 8/2014 | Lavash |
| 8,847,002 | B2 | 9/2014 | Goh et al. |
| 8,961,486 | B2 | 2/2015 | Stewart |
| 2002/0107496 | A1 | 8/2002 | Wang |
| 2002/0120247 | A1 | 8/2002 | Mizutani et al. |
| 2002/0143309 | A1 | 10/2002 | Glasgow et al. |
| 2002/0193766 | A1 | 12/2002 | Gell et al. |
| 2003/0055392 | A1 | 3/2003 | Tagami et al. |
| 2003/0078554 | A1 | 4/2003 | Drevik |
| 2003/0093054 | A1 | 5/2003 | Sierri et al. |
| 2003/0120235 | A1 | 6/2003 | Boulanger |
| 2005/0027278 | A1 | 2/2005 | Mizutani et al. |
| 2005/0131369 | A1 | 6/2005 | Benson |
| 2005/0256472 | A1 | 11/2005 | Tsutsui |
| 2006/0135930 | A1 | 6/2006 | Mizutani et al. |
| 2006/0135934 | A1 | 6/2006 | Gilbert |
| 2006/0142725 | A1 * | 6/2006 | Fujikawa ........... A61F 13/47218 604/385.04 |
| 2006/0178652 | A1 | 8/2006 | Miller, III |
| 2006/0184150 | A1 | 8/2006 | Noel |
| 2007/0156110 | A1 | 7/2007 | Thyfault |
| 2008/0132870 | A1 | 6/2008 | Nelson |
| 2008/0172019 | A1 | 7/2008 | Chien |
| 2009/0099539 | A1 | 4/2009 | Periman |
| 2009/0240225 | A1 | 9/2009 | Noda et al. |
| 2010/0069868 | A1 | 3/2010 | Noda et al. |
| 2010/0069874 | A1 | 3/2010 | Noda et al. |
| 2010/0152692 | A1 | 6/2010 | Ong et al. |
| 2010/0280475 | A1 * | 11/2010 | Kudo ................. A61F 13/47218 604/380 |
| 2011/0257619 | A1 | 10/2011 | Tosado et al. |
| 2012/0035567 | A1 | 2/2012 | Kuroda et al. |
| 2012/0071851 | A1 | 3/2012 | Vasic |
| 2013/0042394 | A1 | 2/2013 | Wexler |
| 2013/0060218 | A1 * | 3/2013 | Kudo .................... A61F 13/495 604/379 |
| 2013/0165886 | A1 | 6/2013 | Glaug et al. |
| 2013/0226123 | A1 | 8/2013 | Kudo et al. |
| 2014/0296814 | A1 | 10/2014 | Gray et al. |
| 2017/0354549 | A1 | 12/2017 | Cho et al. |
| 2017/0354550 | A1 * | 12/2017 | Park .................... A61F 13/5116 |

FOREIGN PATENT DOCUMENTS

| | | |
|---|---|---|
| DE | 102010010680 A1 | 9/2011 |
| EP | 0210969 A2 | 2/1987 |
| EP | 0735850 B1 | 4/1999 |
| EP | 1048277 A2 | 11/2000 |
| EP | 0967951 B1 | 5/2003 |
| EP | 1349525 B1 | 4/2005 |
| EP | 1016393 B1 | 3/2007 |
| JP | 62-056025 U1 | 4/1987 |
| JP | 07-231904 A | 9/1995 |
| JP | 2002-159534 A | 6/2002 |
| JP | 2002-301097 A | 10/2002 |
| JP | 2008-023248 A | 2/2008 |
| JP | 4925632 B2 | 5/2012 |
| JP | 4939026 B2 | 5/2012 |

(56) References Cited

FOREIGN PATENT DOCUMENTS

| | | |
|---|---:|---|
| JP | 4976066 B2 | 7/2012 |
| JP | 5244301 B2 | 7/2013 |
| JP | 5551424 B2 | 7/2014 |
| KR | 10-2012-0061497 A | 6/2012 |
| WO | WO 1990/004956 A1 | 5/1990 |
| WO | WO 1992/007535 A1 | 5/1992 |
| WO | WO 1995/008972 A1 | 4/1995 |
| WO | WO 1996/038110 A1 | 12/1996 |
| WO | WO 1997/007763 A1 | 3/1997 |
| WO | WO 1997/007764 A1 | 3/1997 |
| WO | WO 1997/014389 A1 | 4/1997 |
| WO | WO 2002/062278 A1 | 8/2002 |
| WO | WO 2003/075813 A1 | 9/2003 |
| WO | WO 2008/090756 A1 | 7/2008 |
| WO | WO 2009/145466 A2 | 12/2009 |
| WO | WO 2011/122710 A1 | 10/2011 |
| WO | WO 2012/057332 A1 | 5/2012 |
| WO | WO 2012/132488 A1 | 10/2012 |
| WO | WO 2012/155316 A1 | 11/2012 |
| WO | WO 2014/191921 A1 | 12/2014 |

\* cited by examiner

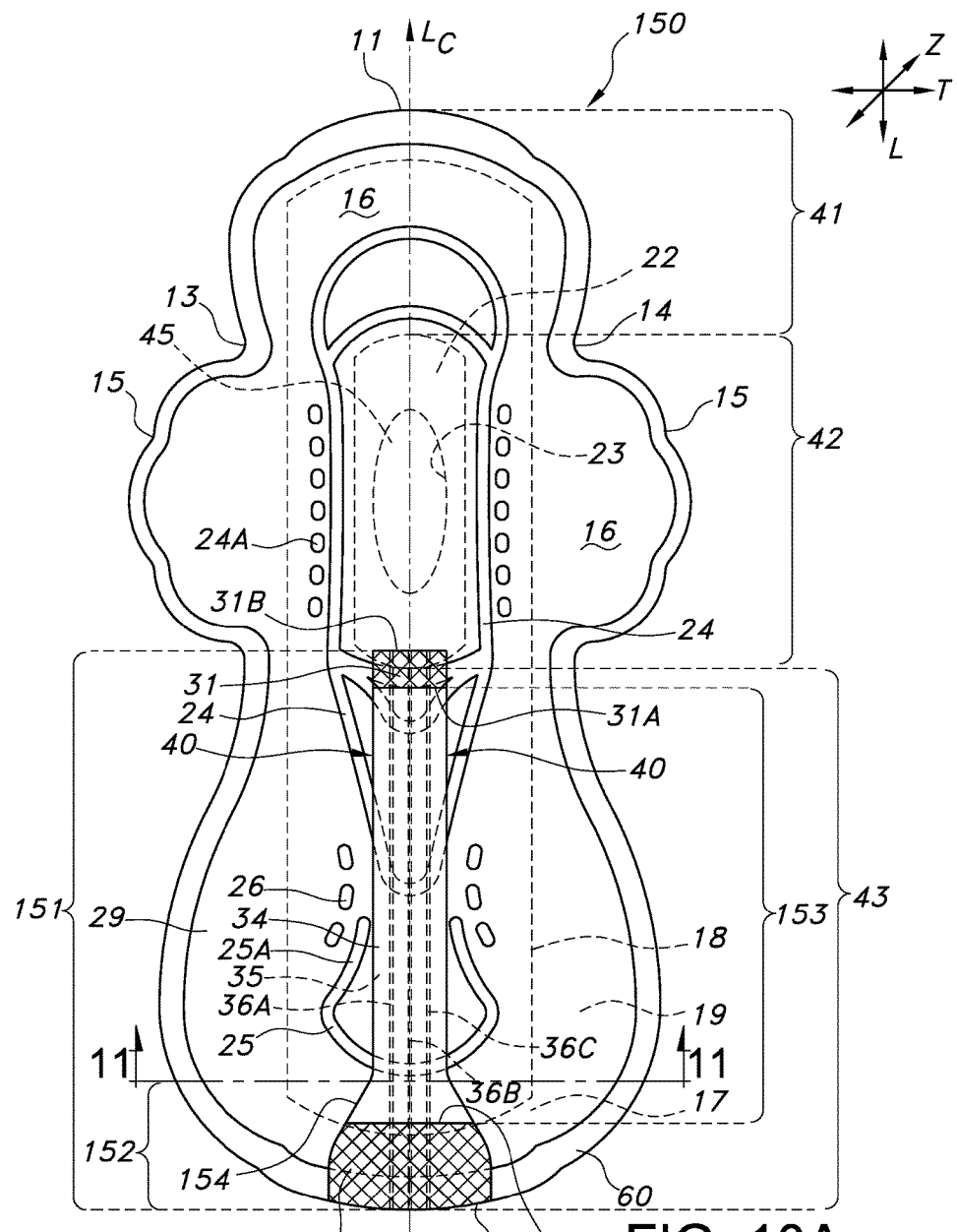
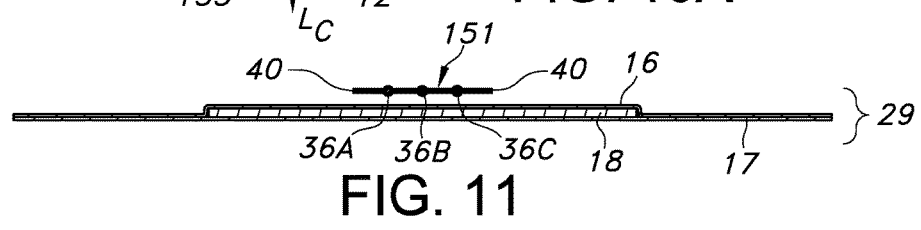
FIG. 10A
FIG. 11 ly invention is generally directed to personal
ABSORBENT ARTICLE WITH FLAT-BACK PROTECTION FEATURE This application claims the benefit of priority from U.S. Provisional Application No. 62/301,338 filed on 29 Feb. 2016, the contents of which are incorporated herein by reference.

FIELD OF THE INVENTION

The present invention is generally directed to personal care absorbent articles, especially for use over an extended time frame. In particular, the present invention is directed to extended-wear absorbent articles for absorption of body exudate while a wearer of such articles is in either a supine, fetal, or side sleeping position, such as for example, while a wearer is experiencing menorrhea during multiple overnight hours. More specifically, the present invention is directed to absorbent personal care articles which include an additional elevated layer above a topsheet layer, which additional elevated layer may include an elastic component.

BACKGROUND OF THE INVENTION

So as to provide protection for consumers who experience conditions that lead to the release of body exudate (such as for example, incontinence or menorrhea), consumer product manufacturers have developed a wide range of personal care absorbent articles to reduce or eliminate undergarment, garment, and/or bedding soiling. Such traditional absorbent articles, often described as "pad" or "absorbent garments" (i.e. pants or diapers), are worn either in the crotch region of undergarments or garments, or alternatively, in place of the undergarments themselves. Such absorbent articles generally include a liquid permeable topsheet layer, through which body exudate passes into the absorbent article, a liquid impermeable backsheet layer, which serves as a barrier to keep body exudate from passing out of the article after it has collected within the article, and an absorbent layer that is both sandwiched and sealed between the liquid permeable topsheet layer and liquid impermeable backsheet layer, for retaining the body exudate in the article. Not surprisingly, these traditional absorbent articles are most effective for preventing leakage of exudate when they are held in close proximity to a wearer's body, or when they at least include barrier-type structures adjacent their lateral side edges that are sealed against a wearer's body, so as to prevent wicking of exudate along a wearer's body surfaces and beyond the coverage of the articles. However, the reliable collection of body exudate while an article wearer is sleeping, presents its own set of challenges, as wearers of such articles frequently move about between supine, prone, and/or body side positions, and their undergarments or sleepwear are not always held tightly against their bodies. As a result of these constantly changing sleep positions, traditional pads or diapers can become physically separated or dislodged from the wearer's body (i.e. with spaces forming between the article and the wearer's body), leading to fluid leakage and subsequent undergarment or bedding staining. Furthermore, pad-type articles are often planar in shape, and do not conform to the dips and curves of a wearer's anatomy, leading to at least peripheral gaps in contact between the article and the wearer. The wearer of such articles are likely to be unaware that leakage is occurring, and the leakage problem may be exacerbated over the course of a night as traditional absorbent pads and panty liners move about, such as from side to side as the crotch region of a wearer's undergarment shifts, and potentially twists or turns the absorbent article out of its most desirable position with the wearer's movements.

So as to address these and other fluid capture challenges of extended-wear absorbent articles, manufacturers have developed a wide range of extended-wear, or "overnight" absorbent article features. For example, absorbent pads have been designed with either greater absorbency levels, targeted absorbency locations in the pad, and/or extended length and width dimensions in the region of the pad that is to be placed immediately adjacent the wearer's buttocks, in order to provide a larger exudate collection surface. A description of asymmetrical pads can be seen for example, in international patent publication number WO95/15139 to Unger et al. However, even with such targeted absorbency features and enlarged dimensions, such products still tend to separate from a wearer's body during sleep movements, potentially leading to leakage. Further, article leakage also continues to be an issue for consumers particularly along the curved portions of a wearer's anatomy, where exudate may wick or flow beyond the peripheral edges of the relatively planar absorbent article surfaces, since such articles are not sealed tightly to the wearer's anatomy at these locations. This leakage may occur along the buttocks or so-called intergluteal cleft region (i.e adjacent the wearer's back) while shifting sleeping positions. The intergluteal cleft region is that region of a consumer's anatomy between the end of their back and the wearer's anal region (between the buttocks), with the gluteal cleft being the sulcus between the wearer's buttocks. There is therefore still a need for an extended-wear, absorbent article which generally stays in place over the course of multiple hours during a night, and which provides for capture of body exudate despite being exposed to a wide range of wearer positions and/or physically separating from a wearer's body adjacent curved body features.

In order to specifically address leakage of body exudate from absorbent articles along the buttocks and intergluteal cleft region of a wearer, absorbent articles having a freely extending, tail-like feature or flap (and which is also absorbent) have been developed, which tail-like feature is configured to move about with the movement of the underside of the buttocks of a wearer as he/she changes position. An example of such extended length string, tail, or flap is described for instance, in International Patent Publication WO 02/062278 to Mok and European Patent Publication EP 1048277 to Calia. However, such unattached tail may twist and turn over time, leading to discomfort during a wearer's movements, and may also become positioned in ineffective fluid-capture locations over the course of an evening, thereby also leading to eventual exudate leakage.

In order to provide for increased absorbency or fluid capture, particularly along the intergluteal cleft region of a wearer, absorbent pads have also been developed which include an elevated, centrally positioned absorbent layer that essentially rises above a base pad upper-most surface, along a substantial length of the base pad. The centrally positioned absorbent layer is biased towards a wearer's anatomy as a result of elastic tension in the layer. Such elevated absorbent layer designs may be seen for instance, in United States Patent Publications 2002/0120247 and 2006/0135930 to Mizutani et al. and U.S. Pat. No. 6,293,935 to Kimura et al., U.S. Pat. No. 6,296,628 to Mizutani, U.S. Pat. No. 6,471,682 to Kashiwagi, and U.S. Pat. No. 8,439,886 to Hashino et al. However, many of such designs require the inclusion of costly absorbent material along a large portion of the upper layer, or extended length sheet/elastic material which is forcibly maintained in close proximity to the body of the wearer over the time of wear (as a result of elastic tension in the layer), thereby increasing the possibility of wetness sensation being felt by the wearer across their anatomy, and for a prolonged timeframe. Such elevated layer typically extends from a location near the back abdominal region of the wearer, across the wearer's crotch and to the front abdominal region. As a result, such elastically biased layer may lead to frictional discomfort over the course of wear.

Still further designs have been described in the patent literature, which provide for only partially-elevated fluid capture features. Such partially-elevated features include either a raised, discrete absorbent protrusion, typically having a triangular cross-sectional shape so as to fit within the intergluteal cleft region of a wearer, or a raised central hollowed protrusion, in order to more closely adhere to the intergluteal cleft shape along much of the wearer's crotch region. An example of this peaked, hollow feature is illustrated for instance, in the description of U.S. Pat. No. 8,048,049 to Fujikawa et al. Such central peaked feature may also lead to discomfort over time, as the article maintains a pressed, skin-contacting configuration with a wearer across sensitive anatomical features. Further, such articles do not completely address problems of leakage of fluid from the upper intergluteal cleft region (i.e. flat area) immediately adjacent the back of the wearer.

Finally, further designs have been described in the literature which provide for partially elevated and flattened, fluid capture features located towards the back end of an absorbent article. Such may be seen for example in United States Patent Publication 2013/0060218 to Kudo et al., Korean Patent Publication 10-2012-0061497 to Hwang et al., Japanese Patent Nos. JP5244301B2 to Kamiyama et al. and JP4939026B2 to Kuroda et al. However, even with such flattened, elevated features, there is still a need for absorbent articles which demonstrate an increased ability to stay in place, and which provide for reliable exudate collection despite the wearer shifting position and the article being adjacent to curves on the wearer's anatomy.

Many of the foregoing absorbent articles include elastic components as part of their structures, which are designed in conjunction with separate absorbent layers to capture fluid from the intergluteal cleft region. However, the folding of such articles for storage prior to use can negatively impact the long term efficacy of such elastic components, as they may be stored under pressure (in less than effective folded configurations) or exposed to unfavorable embossing steps during article manufacture, and prior to folding. There is therefore a need for extended-wear absorbent articles which may be easily folded for storage prior to use, without impacting the elastic functionality of article structures.

SUMMARY OF THE INVENTION

The absorbent article of the present is capable of capturing body exudate while a wearer of the article is in a supine, prone, or fetal position, and incorporates a flat-back, protection feature, which feature is formed from an elongated planar structure that rises in use, above a base-pad structure, in order to direct body exudate that may be situated within or adjacent to a wearer's intergluteal cleft region to the primary absorbent layer of the article. Accordingly, an absorbent article of the present invention is provided having a base structure for retaining body exudate that includes a liquid permeable topsheet layer, a liquid impermeable backsheet layer, and an absorbent layer sandwiched and sealed between the topsheet layer and said backsheet layer. The absorbent article further includes an elevatable structure positioned along the central longitudinal axis that is capable of separating in part from the topsheet layer of the base structure in the back region. The elevatable structure includes a first fastening region attached to the topsheet layer in the middle region of the article and a second fastening region attached to the topsheet layer in the back region. Between the first and second fastening regions, the elevatable structure includes an unattached region having an unattached length extending continuously there between. The elevatable structure is relatively planar in that it does not include any transverse axis bend that extends uniformly along the unattached region on the longitudinal axis between the first and second fastening regions. The transverse axis width of the elevatable structure may be the same along the entire longitudinal axis or may vary. In certain embodiments, the elevatable structure may be wider towards at the back end of the article. The elevatable structure may, optionally, in certain embodiments comprise an elastic, hydrophobic and/or non-absorbent material.

The absorbent article further includes embossment features that extend longitudinally on the base structure, and which are symmetrically placed laterally beyond the longitudinal side edges of the elevatable structure and the central longitudinal axis. The embossment features each include a spatial gap along the longitudinal direction being positioned adjacent the unattached region. Further, any embossment features that cross the central longitudinal axis do so either in locations in which said elevatable structure is not present, or alternatively, only in one or both of the first or second fastening regions. In certain embodiments, the additional embossment features may include a spatial gap between them including, for example, along the transverse axis. In still other embodiments, the embossment features laterally positioned relative to the elevatable structure include outwardly flared portions. The absorbent article may also optionally include embossed fold lines positioned within the spatial gaps of the embossment features. Additionally, in instances where the elevatable structure includes an elastic material, the additional embossment features may in certain embodiments be positioned at least partially over the elastic material.

BRIEF DESCRIPTION OF THE DRAWINGS

A full and enabling disclosure of the present invention is set forth more particularly in the remainder of the specification, including reference to the accompanying figures, in which:

FIG. 10A illustrates a top plan view of still a further alternative embodiment of an absorbent article having a flat-back, protection feature, shown with the article in an open and uncontracted position.

FIG. 11 illustrates a cross-sectional view of the alternative embodiment of FIG. 10A, at line 11-11.

DEFINITIONS

Figure 1:
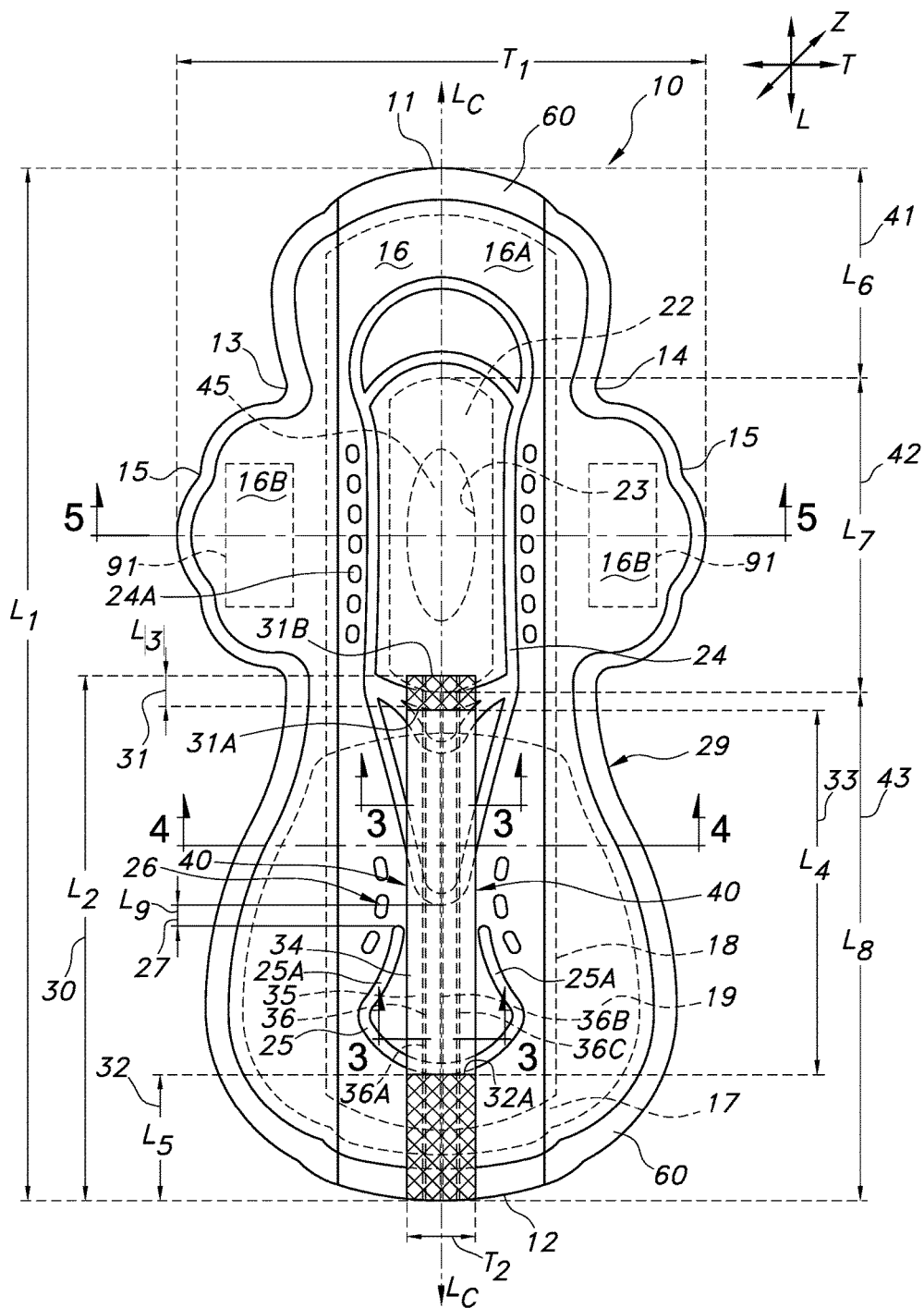
FIG. 1 illustrates a top plan view of an absorbent article having a flat-back, protection feature in accordance with the disclosure, shown with the article in an open and uncontracted position.

As used herein, the term "nonwoven fabric or web" refers to a web having a structure of individual fibers or threads which are interlaid, but not in an identifiable manner as in a knitted fabric. Nonwoven fabrics or webs have been formed from many processes such as for example, meltblowing processes, spunbonding processes, coforming processes, hydroentangling, airlaying, and bonded carded web forming processes (such as through-air bonded carded webs or TABCW, or thermally-bonded carded webs or TBCW).

As used herein, the term "extended wear" refers to an absorbent article that is to be worn over multiple hours, and potentially through various body orientations, such as for example in supine, prone, and side sleeping positions.

As used herein, the terms "elastomeric," "elastic," "elasticized," and "elastically", generally refer to that property of a material or composite by virtue of which it tends to recover (or contract to) its original size and shape (or a portion thereof) after removal of a force causing a deformation. Essentially, an elastomeric material is an extendable material having recovery properties. Suitably, an elastomeric material can be elongated to at least 25 percent of its relaxed original length (percent elongation refers to the increase in the original length of the untensioned material, i.e., 0 percent refers to the original length of the untensioned material) in the direction of an applied biasing force, and which will recover, upon release of the applied force, at least 10 percent of its elongation, and in one embodiment, at least 50 percent of its elongation, but desirably more. It is generally preferred that the elastomeric material or composite be capable of being elongated by from at least about 25 percent of its relaxed original length (i.e., an increase of 25 percent from its untensioned length) to about 200 percent of its relaxed original length, for example preferably from at least about 50 to about 100 percent of its relaxed original length. An elastic material may include a fiber, ribbon, strand, film, foam, laminate, or fabric. The elastic fiber, strand, film, foam, laminate, or fabric could be formed from any suitable material, including but not limited to: natural rubber materials, polymeric materials such as polyurethane, styrenic block copolymers, such as KRATON brand commercial elastomers from Kraton Polymers of Houston, Tex.; polyether ester, such as HYTREL brand materials from E. I. Du Pont De Nemours and Company Corporation Wilmington, Del.; polyether amide, such as PEBAX brand materials, from Atochem Corporation, France; and elastic metallocene-catalyzed materials, such as AFFINITY brand materials, from Dow Chemical, Midland, Mich. Furthermore, elastic fabrics may be formed from preformed polyester-polyurethane copolymer elastic yarns or strands, such as LYCRA brand strands. The elastic materials may be formed into laminates, such as for example, a neck-bonded laminate (NBL) or stretch-bonded laminate (SBL). Methods of making such materials are well known to those skilled in the art and are described in U.S. Pat. No. 4,663,220 to Wisneski et al., U.S. Pat. No. 4,741,949 to Morman et al., U.S. Pat. No. 5,226,992 to Morman, U.S. Pat. No. 8,361,913 to Siqueira at al. and European Patent Application No. EP 0 217 032 to Taylor et al., each of which is hereby incorporated by reference thereto in its entirety, to the extent that it is not inconsistent with this disclosure.

As used herein, the term "stretch-bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered. Such a multilayer composite elastic material may be stretched to the extent that the nonelastic material gathered between the bond locations allows the elastic material to elongate. One type of stretch-bonded laminate is disclosed, for example, by U.S. Pat. No. 4,720,415 to Vander Wielen et al., in which multiple layers of the same polymer produced from multiple banks of extruders are used. Vander Wielen et al. is hereby incorporated by reference thereto in its entirety, to the extent that it is not inconsistent with this disclosure. Other composite elastic materials are disclosed in U.S. Pat. No. 4,781,966 to Taylor, U.S. Pat. No. 4,789,699 to Kieffer et al., U.S. Pat. No. 5,366,793 to Fitts, Jr. et al., U.S. Pat. No. 5,385,775 to Wright, and U.S. Pat. No. 6,969,441 to Welch et al., each of which is hereby incorporated by reference thereto in its entirety, to the extent that it is not inconsistent with this disclosure. Further reference will be had to U.S. Pat. Nos. 4,652,487, 4,655,760, and 4,657,802 to Morman et al., each of which is also hereby incorporated by reference thereto in its entirety, to the extent that it is not inconsistent with this disclosure.

The term "neck-bonded" refers to an elastic member being bonded to a non-elastic member while the non-elastic member is extended and necked (narrowed). "Neck-bonded laminate" refers to a composite material having at least two layers in which one layer is a necked, non-elastic layer and the other layer is an elastic layer. The layers are joined together when the non-elastic layer is in an extended and necked condition. Examples of neck-bonded laminates include those described in U.S. Pat. Nos. 4,965,122, 4,981,747; and U.S. Pat. No. 5,336,545 to Morman, each of which is hereby incorporated by reference thereto in its entirety, to the extent that it is not inconsistent with this disclosure. The term "necked stretch bonded" refers to an elastic member being bonded to a non-elastic member while the non-elastic member is extended and necked and the elastic member is at least extended. "Necked stretch bonded laminate" refers to a composite material having at least two layers in which one layer is a necked, non-elastic layer and the other layer is a stretched, and sometimes necked, elastic layer. The layers are joined together when in their extended (and necked) conditions. Examples of necked stretch bonded laminates are described in U.S. Pat. Nos. 5,114,781 and 5,116,662 to Morman, each of which is hereby incorporated by reference thereto in its entirety, to the extent not inconsistent with this disclosure. Further examples of laminates that may be used in accordance with this disclosure are described in U.S. Pat. No. 7,018,369 to Van Gompel et al. which is hereby incorporated by reference thereto in its entirety, to the extent that it is not inconsistent with this disclosure. It should be appreciated at least from these foregoing references that elastic laminates for use with the flat-back, protection feature of this disclosure may include elastic layers that are formed from elastic fibers, ribbons, yarns, strands, nonwoven webs, foams (such as open and closed cell foams), films (such as nonapertured or apertured films), or combinations thereof. Nonwoven webs that may be bonded to elastic layers include for example, spunbond, meltblown, and TABCW webs.

As used herein, the term "hydrophobic" shall refer to a material having a contact angle of water in air of at least 90 degrees. The terms "hydrophilic" and "wettable" are used interchangeably to refer to a material having a contact angle of water in air of less than 90 degrees. The phrase "more hydrophilic" shall refer to a material having a relatively lower contact angle. The phrase "more hydrophobic" shall refer to a material having a relatively higher contact angle. Hydrophobicity and hydrophilicity can both be the result of the inherent properties of the composition making up a material. For example, polyolefinic and/or elastomeric polymers are typically hydrophobic, while cellulosic materials are typically hydrophilic. Alternatively, such properties may be the result of coatings that have been added to base substrates, or additives within the materials making up a particular layer.

For the purposes of this application, contact angle measurements can be measured using a Cahn SFA-222 Surface Force Analyzer System, or a substantially equivalent system. Contact angles can be determined as set forth in Neumann, A. W., and R. J. Good, "Techniques of Measuring Contact Angles," Chapter 2, Surface and Colloid Science—Experimental Methods, Vol. 11, edited by R. J. Good and R. R. Stromberg, Plenum Press, 1979, pp. 31-91, which is hereby incorporated by reference in a manner that is consistent herewith. For coated substrates, contact angle measurement may be made in accordance with ASTM D-7334, titled "Standard Practice for Surface Wettability of Coatings, Substrates and Pigments by Advancing Contact Angle Measurement". Such advancing contact angle measurement is preferred unless otherwise noted.

For the purposes of this application, the terms "embossment", "embossing feature," "embossment pattern", and "embossment feature" shall be used synonymously and shall refer to a structural feature formed by the compression of one or more layers within an absorbent article, by heat, pressure, ultrasonic bonding techniques or a combination thereof, which process presses a discrete recess (such as a continuous channel, or discontinuous series of discrete shapes) into the one or more layers of the absorbent article. Such embossing process may lead to increased density of the layer(s) beneath the embossment feature and may be used to improve liquid handling, article shaping, or a combination thereof. Such embossing process may lead to multiple elevations within the embossment feature. Further, such embossing process may produce an embossment feature which includes relatively large channels or shapes, relatively small "microembossed" shapes, or a combination thereof, such as relatively large channels or shapes that also include microembossed patterns across their dimensions. Such embossing may be accomplished by known embossing techniques, such as for example, running a material or article which is to be embossed, through a pair of patterned and smooth anvil rolls, or patterned and coated anvil rolls. Embossing techniques are described in U.S. Pat. No. 5,795,345 to Mizutani et al., U.S. Pat. No. 7,145,054 to Zander et al., and U.S. Pat. No. 8,998,871 to Kuroda et al., each of which is hereby incorporated by reference thereto in its entirety, to the extent not inconsistent with this disclosure.

As used herein, the terms "comprise", "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Similarly, the terms "include", "includes", "has" and/or "have", and derivatives thereof, are intended to be interpreted as the word "comprise", and are intended to be open-ended terms that specify the presence of any stated features, elements, integers, steps, or components, but do not preclude the presence or addition of one or more other features, elements, integers, steps, components, or groups thereof.

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. For the purposes of this application, like features may be represented by like numbers between the figures. While not illustrated in most figures except where additional placement emphasis is desired, it should be understood that traditional article construction, or garment adhesive (or other bonding technology) is to be used to fasten the various layers of the described articles together, or to fasten the articles to a wearer's garments or undergarments in the crotch region. Such adhesive or other bonding technology is desirably placed or practiced so as not to interfere with the flow of body exudate through the liquid permeable and absorbent layers of the article, or the primary functionality of the adhered layers. Contemplated construction bonding techniques include for example, various types of adhesive (such as hot melt adhesive), ultrasonic bonding, pressure bonding, needling, stapling, and thermal bonding techniques, or a combination thereof. Contemplated garment adhesive include various forms of pressure-sensitive adhesive such as those formed from hot-melt adhesive and which are traditionally used to adhere absorbent articles to undergarment surfaces.

The absorbent article of the present disclosure incorporates a flat-back, protection feature, which feature is formed from an elongated planar structure that rises in use, above a base-pad structure in order to direct body exudate that may be situated within or adjacent to a wearer's intergluteal cleft region, to the primary absorbent layer of the article (in a base-pad structure). Such liquid transference is desirably accomplished without the addition of costly absorbent material (such as cellulosic materials and/or superabsorbent material) and relies on the hydrophobicity of the flat-back, protection feature (or portions thereof) to keep body exudate moving along the length of the article. The flat-back protection feature may include some hydrophobic materials in one embodiment, but not be fashioned entirely of hydrophobic materials. For example, a nonwoven layer that has some hydrophilic properties, may be fashioned onto or about an elastic material. The flat-back protection feature provides leakage protection to a wearer of such article, and particularly in a location adjacent a wearer's curved anatomy of the intergluteal cleft. The flat-back protection feature also is positioned along the absorbent article such that in use, it prevents the article from shifting significantly within a wearer's undergarments during the shifting movements of a person sleeping. The flat-back, protection feature is combined with a variety of other article shaping structures, such as outwardly flared embossment features lateral to the longitudinal side edges of the flat-back, protection feature, outwardly flared discontinuous embossment features, outwardly flared peripheral shapes of the feature at the article back end, and outwardly flared embossment features on the flat-back, protection feature itself, to enhance the ability of the article to make predictable contact with a wearer's anatomy while the wearer is sleeping, and also, to provide integrity to the flat-back, protection feature during use. By use of a discrete, generally flattened feature adjacent to only the intergluteal cleft region of a wearer, the absorbent article avoids skin irritation that may result from a more pronounced vertical protrusion of an absorbent article and one that extends along substantially the entire absorbent article length. Further, by use of selectively positioned embossment features laterally adjacent to the flat-back protection feature, and on the flat-back, protection feature itself at attachment locations, such article may be easily folded for storage until needed, with reduced negative impact to the elastic functionality of the flat-back, protection feature. Finally, by use of selectively positioned embossment features on the flat-back, protection feature itself, such feature may be provided with additional strength in high stress structural areas where the feature makes continuous contact with the back of a wearer. For example, such embossments may help accomplish multiple objectives, such as the securement of feature ends to a topsheet without raised or rough edges, as well as helping to define fold lines.

If such flat-back, protection feature includes one or more elastic components, the elasticity of the flat-back, protection feature allows the feature to rise above the absorbent pad base structure throughout use, and to continuously adjust (be biased) towards a wearer's anatomy as the wearer's body separates from the article during sleep, so as to fill the gap of the intergluteal cleft region of the wearer, even in the flat region immediately adjacent the wearer's back. The flat-back, protection feature enables the absorbent article to stay in place (and prevent the article from moving from side to side, even as the crotch region of the wearer's undergarments moves during shifting sleep positions).

The flat-back, protection feature is only elevated adjacent the back portion of the absorbent article, thereby providing for targeted body contact of the feature without the need for excess and costly material across the full length of the absorbent article (unless desired). Given that the flat-back, protection feature is fashioned in one embodiment, from primarily hydrophobic fibrous and stranded materials, it readily moves body exudate such as menses along its length to the absorbent layer of a base-pad structure, without retaining body waste itself. Such hydrophobicity reduces rewet sensations over the course of article usage.

FIG. 1 illustrates a top plan view of an absorbent article 10 having a base structure 29 and a flat-back, protection feature 30 including longitudinally directed side edges 40, in accordance with the disclosure. For the purposes of simplicity, each of the illustrations show the absorbent article as an overnight-style, feminine hygiene pad. However, it should be recognized that other absorbent article product categories may also take advantage of the flat-back, protection feature of the disclosure. For instance, such features may similarly be used on adult incontinence articles as well. Since the illustrated absorbent articles are overnight-style, feminine hygiene pads, the base structure 29 will be referred to in the remainder of the disclosure as the base-pad structure 29. The pad in FIG. 1 is shown in an partially open (unfolded) configuration, but one that is relaxed such that the flat-back protection feature is in at least a partially contracted state. The flat-back protection feature is planar, or generally planar when in a relaxed and contracted state, but flattens out even further (if elastic) as the product is maintained under tension in a fully opened state (only for elastic embodiments).

The illustrated absorbent article 10 (overnight-style, feminine hygiene pad) of the disclosure and its various layers, has a length along a longitudinal axis L (and a central longitudinal axis Lc), a width along a transverse axis T perpendicular to the longitudinal axis L, and a depth along a depth axis Z, orthogonal to both the longitudinal L and transverse T axis. The absorbent article 10 includes a front end 11 for placement adjacent the front abdominal region (such as adjacent a wearer's pubic area), and an opposing back end 12, for placement adjacent the back abdominal region of a wearer, and desirably that location of a wearer's anatomy in which the buttocks intersect with the lower back (intergluteal cleft region). The absorbent article 10 further includes two opposing, absorbent article longitudinally directed side edges 13, 14, which extend between the opposing front and back ends 11, 12. Optional wings or flaps 15 may project from each of the opposing, longitudinally directed side edges 13, 14, for wrapping about the crotch edges of a wearer's undergarments during article use. As noted, the absorbent article 10 includes a distinct base-pad structure 29, and a flat-back, protection feature 30 (located vertically above the base-pad structure 29 along the article depth axis Z), and which is attached to the base-pad structure at least at two spaced-apart attachment locations 31, 32.

The base-pad structure 29 itself has at least one liquid permeable topsheet layer 16, a liquid impermeable backsheet layer 17, and one or more absorbent core layers 18, 19, sandwiched and sealed between the respective topsheet and backsheet layers 16, 17. The one or more absorbent core layers 18, 19 function as the body exudate retention layer(s) of the absorbent article 10 (in the base-pad structure 29). While not shown in the figures, the absorbent article 10, may include several additional functional layers between the topsheet layer 16 and the absorbent core layer 18, such as for example a surge, fluid intake, fluid transfer, and fluid distribution layer that are known in the art.

Figure 7:
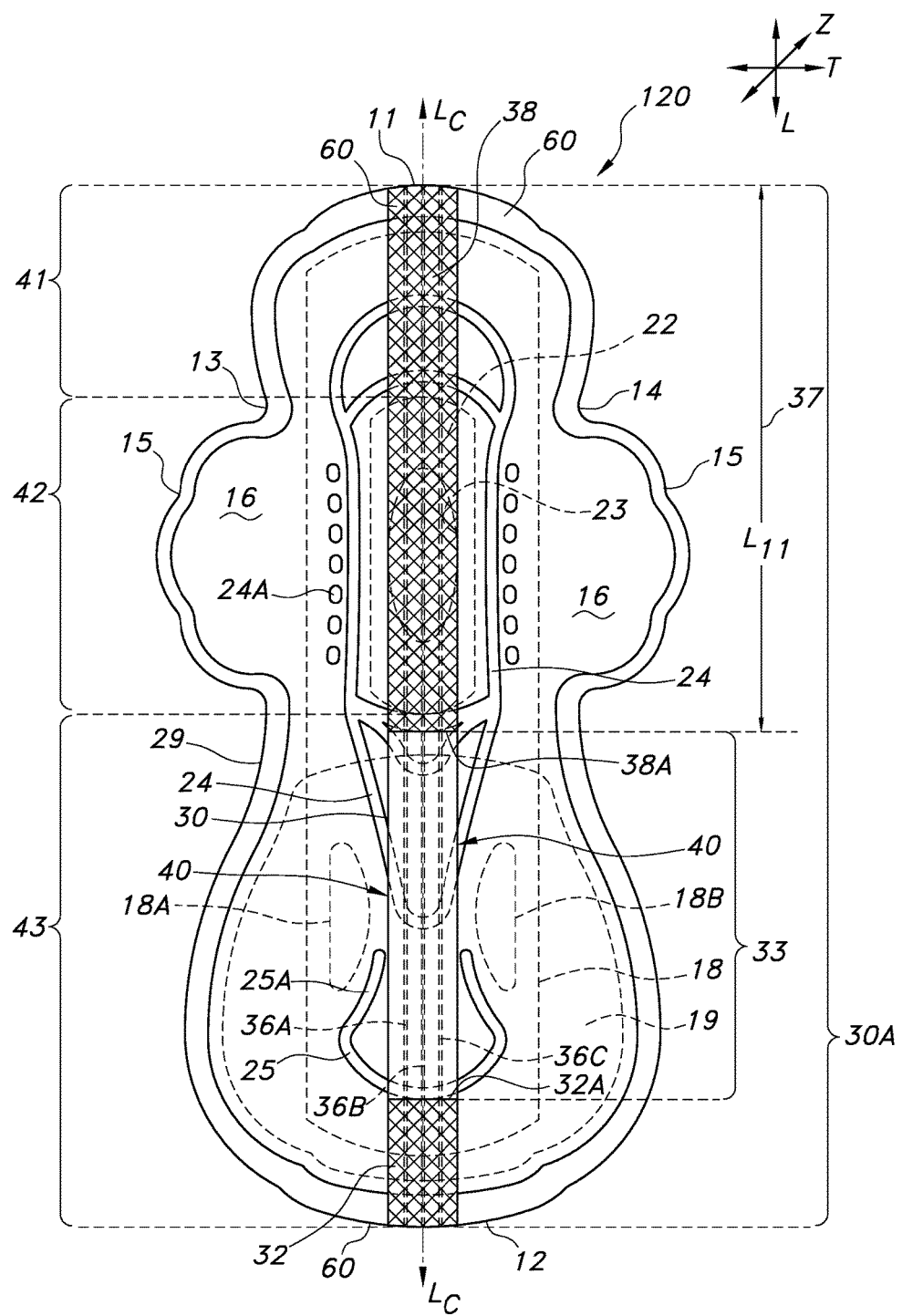
FIG. 7 illustrates a top plan view of a still a further alternative embodiment of an absorbent article having a flat-back, protection feature, shown with the article in an open and uncontracted position.

As particularly seen in FIG. 1, the absorbent article 10 may include a relatively narrow absorbent core layer 18 vertically adjacent to a relatively wider absorbent core layer 19, with the wider absorbent core layer 19 being positioned at least adjacent the article back end 12. Alternatively, the absorbent core layer may only include parallel side edges which extend inward of the longitudinally directed side edges 13, 14 of the absorbent article (not shown). The topsheet and backsheet layers 16, 17 are in one embodiment, of the same dimensions, and are sealed together at their peripheral edges along a peripheral seal region 60. Such sealing may be accomplished via known methods such as for example, through ultrasonic, adhesive, or thermal bonding techniques. The liquid permeable topsheet layer 16 may comprise only one layer (not shown) that extends continuously across the entire longitudinal and transverse dimensions of the absorbent article 10 base-pad structure (as seen in FIG. 7 for example), and which is generally of the same dimensions as the underlying backsheet layer 17, or alternatively, may include a central, longitudinally directed liquid permeable topsheet layer 16A flanked along its longitudinally directed side edges by two opposing and separated, side liquid permeable topsheet layer sections 16B (as seen in FIG. 1). Such multiple layer topsheet configuration, also known as a "dual" cover or bicomponent topsheet layers, may provide different functionality or surface "feel" across the transverse axis T of the absorbent article 10 wearer-facing surface. It should be appreciated that each layer has a wearer-facing surface and a garment-facing surface. The wearer-facing surface is that surface of the layer that faces towards the wearer during article use. The garment-facing surface is that surface of the layer that faces towards the garment or undergarment during article use. A wearer-facing surface may not necessarily be the surface that makes actual contact with the skin of the wearer. The garment-facing surface may not necessarily be the surface that makes actual contact with the garment or undergarment of the wearer. The absorbent article also has a wearer-facing surface and a garment-facing surface. In the top plan view of FIG. 1, the wearer-facing surface of the absorbent article faces the viewer.

The base-pad structure 29 may in one embodiment, include one or more discrete embossment features 24, 24A, 25, 26 positioned along the absorbent article longitudinal axis L, and desirably positioned symmetrically about the central longitudinal axis Lc. The embossment features 24, 24A, 25, 26 may in one embodiment, be positioned only within the base-pad structure 29 and not also within or on the flat-back, protection feature 30. In such an embodiment, it may be desirable to emboss the base-pad structure 29 prior to attachment of the flat-back, protection feature in order to avoid damaging any elastic functionality of the flat-back, protection feature 30. Alternatively, the embossment features may only extend laterally outward from the flat-back, protection feature 30 longitudinal side edges 40, and therefore may be applied after attachment of the flat-back, protection feature 30 to the base-pad structure, such as to the topsheet layer 16 (and article) wearer-facing surface. In one embodiment, each of the embossment features 24, 24A, 25, and 26 are longitudinally directed. Alternatively, one or more of the embossment features may extend into both the base pad structure 29 and the flat-back, protection feature 30 as will later be described.

In one embodiment, at least two of the longitudinally adjacent embossment features 24, 25 are separated by a spatial gap 27 between them, such that there is no lateral or longitudinal direction overlap of the embossment features 24, 25 when viewed along the article longitudinal axis. In one embodiment, such spatial gap 27 is present beneath or adjacent the elevated portion 33 of the flat-back, protection feature 30. It should be recognized that by not including a gap in the area 27, (or if too much embossment is employed) the article may be stiff adjacent the flat-back protection feature, impacting wearer comfort over the extended period of use. In certain embodiments, the embossment pattern with gaps provides for a certain stiffness along the transverse direction to keep the base structure stiffer at certain locations, but allows for the article to bend along the longitudinal direction.

Figure 12:
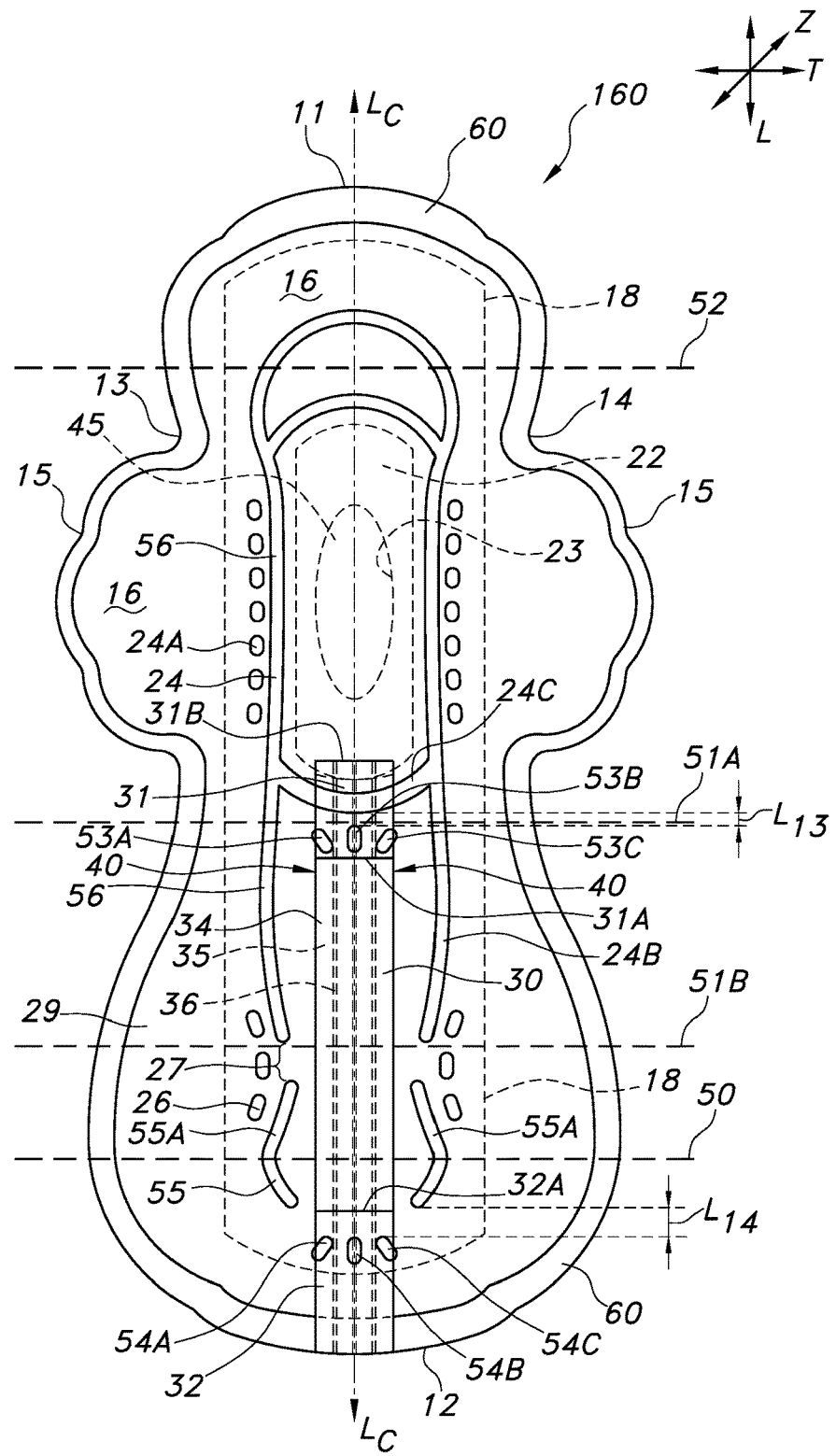
FIG. 12 illustrates a cross-sectional view of still a further alternative embodiment of an absorbent article having a flat-back, protection feature, shown with the article in an open and uncontracted position.

In a further alternative embodiment, at least the embossment feature 25 closest to the back end 12 of the article includes outwardly flared portions 25A, which outwardly flared portions extend laterally (outwardly) beyond longitudinally directed side edges 40 of the flat-back, protection feature 30. The embossment feature 25 may be comprised of two symmetrical, flared and discontinuous channels that do not cross the central longitudinal axis Lc (as seen in FIG. 12), or alternatively, as a single channel that includes two outwardly flared portions and which also extends across the central longitudinal axis Lc.

The absorbent article 10 of the disclosure generally includes three regions along its longitudinal axis, these being a front region 41 immediately adjacent the article front end 11 and extending from the front end 11 to a location adjacent a central fluid deposition region of the absorbent article 10. Such location may also be defined by the location along the longitudinal axis of the article (and closest to the front end) where the wings (if present) join with the longitudinally directed side edges 13, 14 of the absorbent article 10. The central fluid deposition region is the region of the absorbent article 10 which is to be placed directly under the original source of body exudate on the wearer's anatomy, when the absorbent article is in actual use adjacent the wearer's body. At least this region includes the primary absorbent layer 18 of the absorbent article 10. The absorbent article 10 also includes a back region 43, immediately adjacent the article back end 12 and extending to a location adjacent the central fluid deposition region of the absorbent article 10. Such location may also be defined by the location along the longitudinal axis of the article (and closest to the back end) where the wings intersect with the longitudinally directed side edges 13, 14 of the absorbent article 10. The absorbent article 10 also includes a middle region 42 which encompasses the central fluid deposition region, for positioning directly under the source of body exudate from a wearer's anatomy, and situated between the front region 41 and the back region 43. The middle region 42 is in one embodiment, the region that includes any wing or flap projections 15, and may also include an additional layer for the targeted receipt of body exudate, such as layer 22. For instance, as seen in phantom lines in the middle region 42 of the absorbent article 10 of FIG. 1, the middle region 42 includes a fluid collection, fluid transfer, or fluid intake layer 22, which itself defines via an elongated oval edge 23, an annular opening 45 through the layer 22. Body exudate that passes through the liquid permeable topsheet layer 16 above layer 22 and into the annular opening 45, travels directly to absorbent layer(s) 18 subjacent to it, to be absorbed and retained within the absorbent article 10. Such body exudate may also be temporarily stored within the bucket-like feature created by the annular opening 45. The annular opening 45 may be formed from a cut-out portion of layer 22, or by compression which creates a depression in the layer 22. The back region 43 is in one embodiment, longer than either the middle 42 or front 41 regions. The front region 41 is placed in use adjacent the wearer's pubic area, whereas the back region 43 is placed adjacent the wearer's buttocks.

In one embodiment, one embossment feature 24 extends between multiple regions, such as between the front and middle regions, or between the front, middle, and back regions. In one embodiment, a second embossment feature 25 is situated in the back region 42 and includes flared portions 25A, which flare outwardly towards the longitudinally directed side edges 13, 14 of the absorbent article 10. In one embodiment, such flared portions 25A are flared in locations laterally beyond the longitudinally directed side edges 40 of the flat-back, protection feature 30 (as can be seen when viewed from the top plan view of FIG. 1). In one embodiment, a spaced-apart third embossment feature 26 is located laterally beyond the longitudinally directed side edges 40 of the flat-back, protection feature 30, flares outwardly towards the absorbent article, longitudinally directed side edges 13, 14 (when viewed from the top view of FIG. 1), and is also situated laterally adjacent to both the first and second embossment features 24, 25. In one embodiment as illustrated, the first and second embossment features are each continuous embossment channels, whereas the third embossment feature 26 comprises discontinuous embossment features 26, such as discrete dash-like shapes, which when viewed in total, take on an overall flared arc configuration. Each of such embossment features are formed by embossing techniques known in the art, and in one embodiment, extend at least through the topsheet 16 and absorbent core layers 18, such as to compress those layers.

Figure 10B:
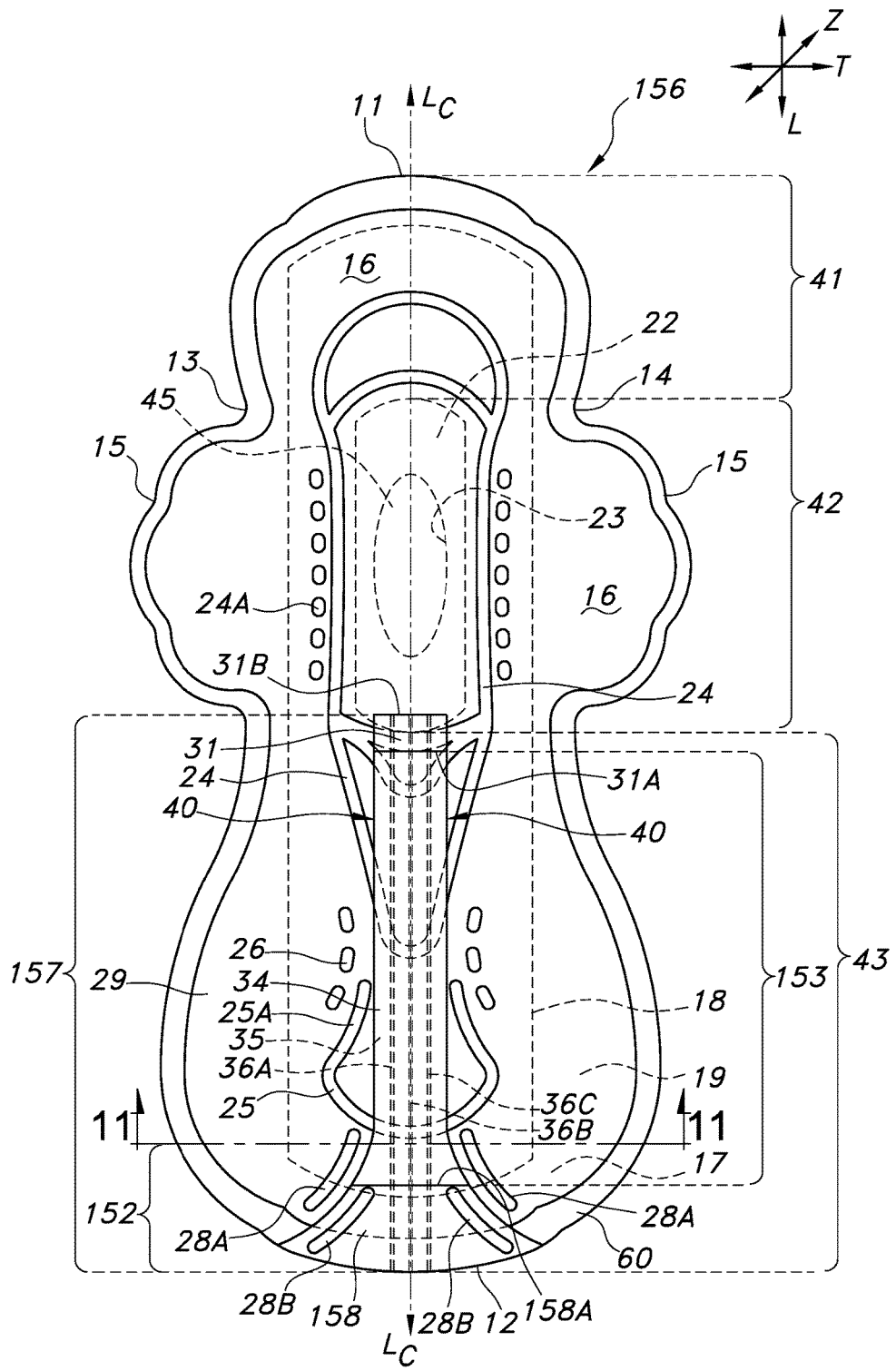
FIG. 10B illustrates a top plan view of still a further alternative embodiment of an absorbent article having a flat-back, protection feature, shown with the article in an open and uncontracted position.

As shown in later Figures, additional embossment features may be located along the longitudinal axis of the absorbent article 10, such as to further facilitate the folding of the absorbent article 10, with little damage to elastic materials of the flat-back, protection feature 30. Still other embossment features as seen in FIG. 10B, may be included to provide additional strength and rigidity to the flat-back, protection feature 30 itself. In yet a further alternative embodiment, as illustrated in later figures, the embossing features are positioned such that they do not impact the ability of the flat-back, protection feature to rise between attachment points. For example, all embossment features may be located lateral to the longitudinal side edges 40 of the flat-back, protection feature. Alternatively, if embossment features cross the central longitudinal axis Lc, they cross the axis either in the front or middle regions 41, 42 of the absorbent article, or in the middle or back regions 42, 42 across the attachment locations 31, 32 of the flat-back, protection feature 30.

While the absorbent article 10 is illustrated as being of asymmetric overall shape so as not to have a central transverse axis and having a central longitudinal axis, such as with a distinctly wider back region 43 than a front region 41 (with the wider back region for placement adjacent the wearer's buttocks), such article may instead be symmetrical about a central transverse axis T (not shown). In such symmetrical article, the length of the front and back regions would be equal (not shown). Alternatively, the front and back regions may have similar shapes, but be of different lengths (not shown).

As illustrated in FIG. 1, the absorbent article 10 includes an elongated flat-back, protection feature 30 (of a planar structure) having a length that extends from the edge, or adjacent the edge of the middle region 42, immediately adjacent the central body exudate deposition region (middle region periphery) to the back end 12 (or adjacent the back end 12). The flat-back, protection feature 30 is in one embodiment, not positioned over much if any of the central body exudate deposition region so as to avoid interfering with the vertical flow of body exudate in the central body exudate deposition region (middle region). In one embodiment, if the absorbent article 10 includes a fluid intake or transfer layer 22 that defines an annular opening 45, such flat-back, protection feature 30 does not extend into or over the annular opening 45.

The flat-back, protection feature 30 is fastened at least at two separated attachment locations to the topsheet layer 16 (or central longitudinally directed topsheet layer 16A, as the case may be), along the central longitudinal axis Lc of the absorbent article 10. The flat-back, protection feature 30 includes a front end directed, fastening region 31 (one attachment location), and a spaced apart, back end directed fastening region 32 (a second attachment location). Between these two fastening regions, the flat-back, protection feature 30 is not attached to any layer of the base-pad structure 29. Along each of the fastening regions 31, 32, the flat-back, protection feature is held tightly to the base-pad structure 29 at least at one point, but desirably at multiple points. The flat-back, protection feature 30 also includes an elevatable (or elevated as the case may be), middle region or portion 33, between the front end directed fastening region 31 and the back end directed fastening region 32, which middle region 33 can be spaced apart from the surface of the topsheet layer 16 (or 16A as the case may be) of the base-pad structure 29, when the absorbent article 10 is being used within the undergarment (or in place of an undergarment) by a wearer of the article. The elevatable middle region 33 actually extends between the closest attachment lines 31A, 32A of the fastening regions 31, 32. In particular, the closest attachment line 31A of the front end directed fastening region 31 and the closest attachment line 32A of the back end directed fastening region 32 form the closest anchoring points of the elevatable middle region 33 to the base-pad structure 29. Such fastening regions may encompass ultrasonic, thermal, adhesive or other bonding devices to secure the feature 30 to the topsheet (and in some embodiments, to lower layers). In a resting and open position, with the absorbent article placed on a flat surface having the backsheet layer 17 facing the flat surface, the absorbent article 10 takes on a decidedly upwardly-curved orientation as the flat-back, protection feature 30 causes the base-pad structure 29 front and back ends to bend upwardly (as seen for example in FIGS. 2A and 2B). This upwardly-curved configuration can be the result of either elastic materials in the flat-back, protection feature contracting the absorbent article front and back ends 11, 12 towards one another, alternatively, the flat-back, protection feature 30 having a length that is shorter than the length of the immediately subjacent base-pad structure 29, or a combination thereof. For example, the flat-back, protection feature 30 may have a contracted length that is shorter than the immediately subjacent base-pad structure. The front and back end directed fastening regions 31, 32 are in one embodiment bonded to at least the wearer-facing surface of the topsheet 16 (or 16A) by traditional bonding techniques, such as for example by ultrasonic, thermal, or adhesive bonding methods or a combination thereof. In one embodiment as shown in FIG. 1, the back end directed fastening region 32 overlaps with the peripheral edge sealing region 60 of the absorbent article 10. In one embodiment, the bonding technique used to bond the peripheral edge sealing region 60, may also bond the back end directed fastening region 32 to the topsheet layer 16 (or 16A as the case may be). In one embodiment, the fastening regions 31, 32 are fastened by ultrasonic bonding. In an alternative, such fastening regions are fastened by adhesive bonding. In a further alternative embodiment, such fastening regions are fastened by a combination of adhesive bonding and thermal bonding/embossment features.

As also shown in the embodiment of FIG. 1, the flat-back, protection feature 30 is comprised of an upper liquid permeable layer 34 which faces the wearer of the article (along the wearer-facing surface of the absorbent article 10), and a lower liquid permeable layer 35, which faces the topsheet layer 16 (or 16A as the case may be). The upper and lower liquid permeable layers 34, 35 may in one embodiment, each be comprised of a single layer, or alternatively multiple layers. Alternatively, they may be formed of one layer that is folded over itself. Alternatively, they may be formed of only one layer in total (such that there are not two distinct layers 34, 35 (not shown). In a further alternative embodiment, one or both of the layers 34, 35 may not be liquid permeable. It is desirably in one embodiment, for the layer or layers 34, 35 to be hydrophobic.

Figure 2A:
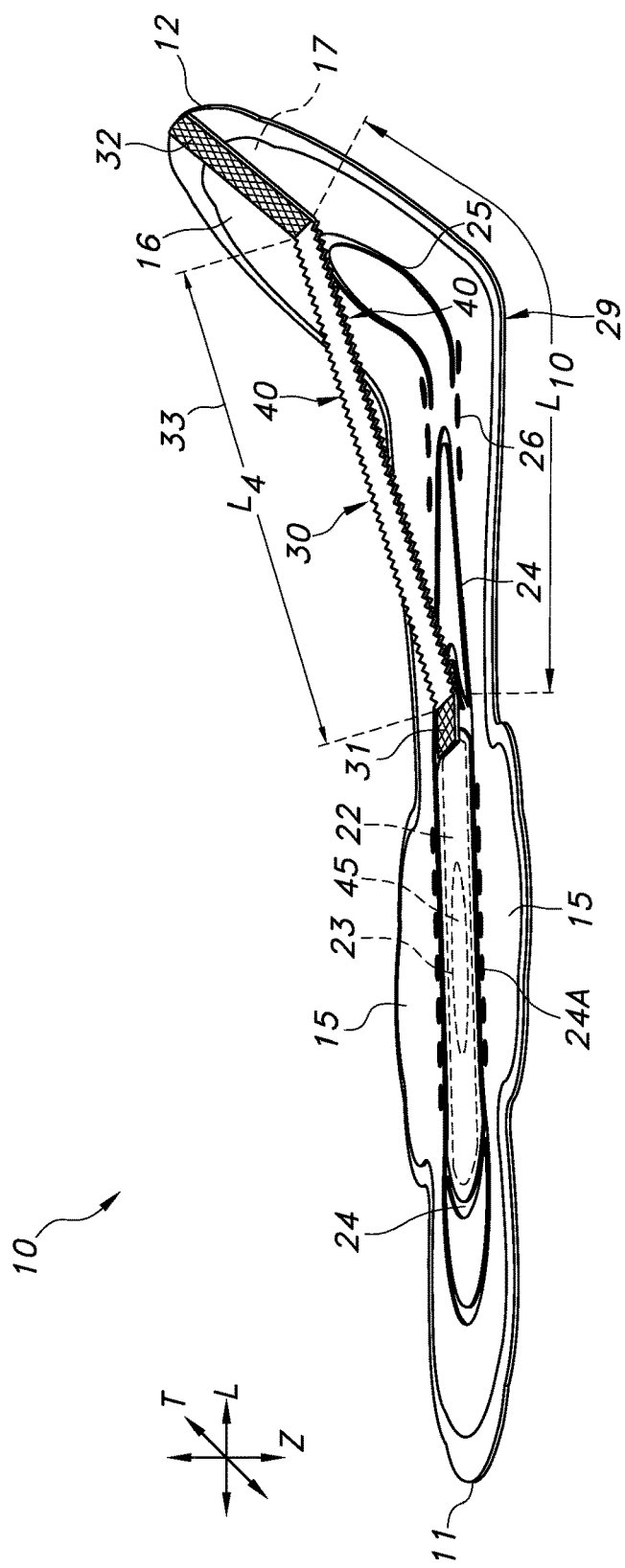
FIG. 2A illustrates a side perspective view of the absorbent article of FIG. 1, in which the flat-back, protection feature is slightly gathered along the article central longitudinal axis, as the article is shown in an open and partially contracted or bent configuration.
Figure 2B:
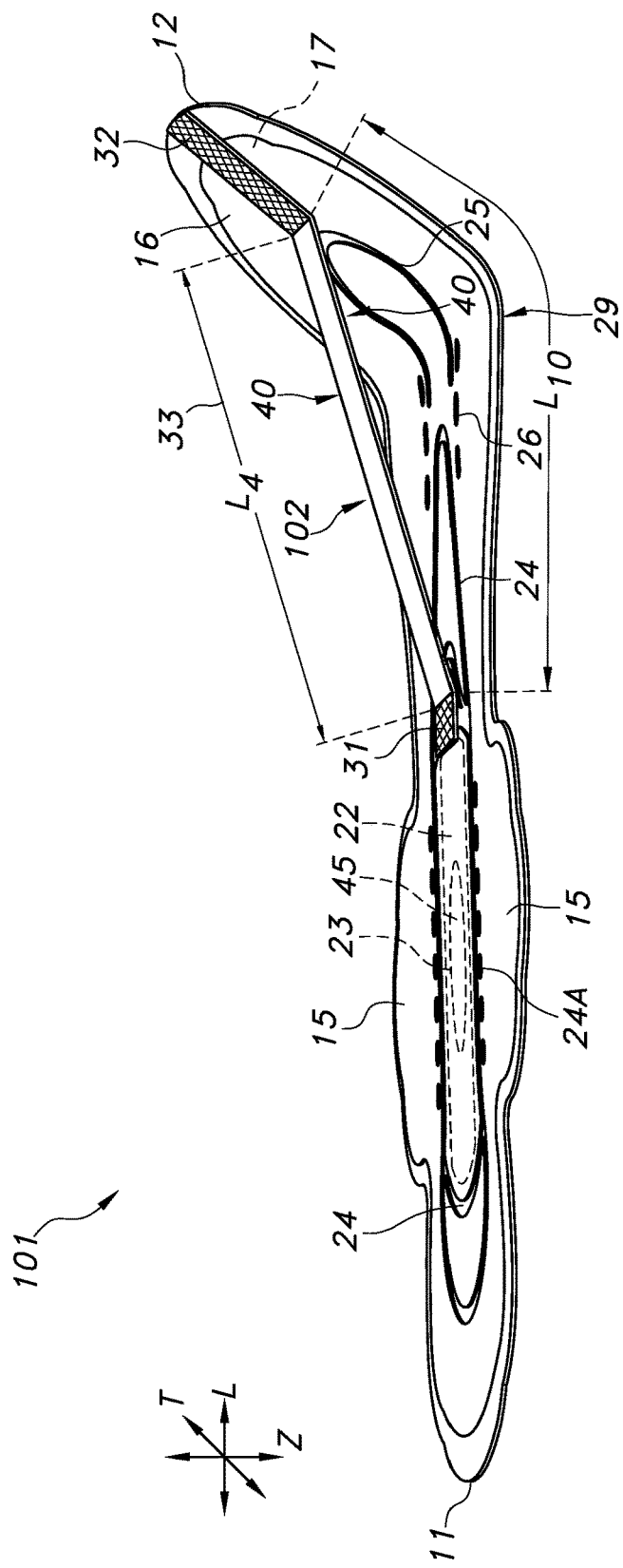
FIG. 2B illustrates a side perspective view of an alternative embodiment of the absorbent article of FIG. 1, in which the flat-back protection feature has a relatively smooth surface topography, as the article is shown in an open and partially contracted or bent configuration.

In the embodiment illustrated, the upper and lower liquid permeable layers 34, 35 envelope an elastic material 36, and in particular, three identically formed, equally spaced-part, dimensioned, and tensioned elastic strands 36A, 36B, 36C which are wrapped by the upper and lower liquid permeable layers 34, 35. The elastic strands 36A, 36B, 36C are in one embodiment, bonded along their length (while in a stretched configuration) to the upper and lower liquid permeable layers 34, 35 such that the liquid permeable layers contract at rest, causing the flat-back, protection feature 30 to take on a slightly gathered topography and the absorbent article 10 itself to take on the upwardly curved configuration shown in FIG. 2A when in a partially open condition and at rest. The slightly gathered topography disappears or is reduced upon the forced flattening of the absorbent article. Since the relaxed configuration of the absorbent article 10 shown in FIG. 2A is upwardly curved (when the article is at rest, not folded, and when the flat-back, protection feature 30 is facing vertically upward), such flat-back protection feature 30 is biased towards an elevated position (at 33) above the subjacent topsheet layer 16, between the fastening regions 31, 32. When the absorbent article is in an inwardly folded configuration (described with respect to the absorbent article 160 of FIG. 12), the flat-back protection feature elevated portion 33, lies against the base-pad structure (topsheet layer 16). This configuration is not shown in the figures.

As noted, the embodiment in FIG. 2A is not in a fully opened state as the back end is slightly curved upward. The term planar shall encompass a material which may include ruffles or gathers as a result of contracted elastic materials in the flat-back, protection feature, but does not include a bend along the transverse axis of the flat-back protection feature that is present along the full longitudinal axis of the flat-back, protection feature or alternatively, is not present along the elevated portion 33 of the flat-back, protection feature.

In one embodiment, elastic material in the flat-back, protection feature 30 is elastic at least along the article longitudinal axis, such that the material extends and contracts along the feature and article longitudinal axis L. The flat-back, protection feature 30 is in one embodiment, fashioned from an elastic nonwoven laminate, such as a stretch bonded laminate, a neck bonded laminate, or a necked stretch bonded laminate, in which an elastic material component (such as one or more elastic strands, ribbons, or sheets) is bonded to one or more inelastic components (such as one or more nonwoven sheets) while the elastic component is in a stretched configuration. Alternatively, such flat-back, protection feature 30 is fashioned entirely from a single elastic sheet, such as from an elastic sheet of film, or an elastic nonwoven material. In one embodiment, such flat-back, protection feature 30 is formed from entirely, or substantially entirely hydrophobic materials. In such an embodiment, body exudate which contacts the feature 30 readily transfers along its length to the middle region 42 or passes directly through it, without being absorbed by the feature 30. In one embodiment, the flat-back protection feature is formed of a laminate of an elastic material and at least one nonwoven sheet. In one embodiment, the flat-back, protection feature is formed from an enveloping sheet of a nonwoven material (such as a spunbond, TBCW, and TABCW), which envelops three parallel strands of LYCRA brand style materials having recovery properties. In one embodiment, strands between about 620 and 940 dTex may be used in the feature.

In either event, the flat-back, protection feature 30 of the absorbent article 10 has a generally flat cross-sectional configuration along its length, such that it does not include uniformly raised portions (along its entire length). That is, the flat-back protection feature 30 is in one embodiment, of generally uniform height across the transverse axis and along its full length, such that it does not take on a peaked or raised elevation (along the middle region 33) either along the central longitudinal axis Lc or along either longitudinal directed side edge 40. It does not form distinct side walls, nor a hollow along its length, as the elastic material or materials in one embodiment, are all generally level across the transverse axis, and in one embodiment along the full length of the flat-back, protection feature. In the case of contracted elastic materials, such elastic materials may include gentle wave-like gathers along the length, but are still generally level across the transverse axis. With the flat-back, protection feature 30 of the disclosure, the feature is in one embodiment either flat across its transverse direction (or slightly gathered as noted) such that the planar surface of its upper liquid permeable layer 34, may lie generally flat against an adjacent body feature or wrap about a curved portion of a wearer's anatomy. This flattened aspect, across the full width and desirably, length of the flat-back, protection feature 30, is evident particularly in FIGS. 3 and 4, which illustrate cross-sectional views of the flat-back, protection feature 30 at three separate locations along its elevated region or portion (33) length. The flattened aspect across the full length of the flat-back, protection feature provides comfort to wearers of the articles, no matter their individual body sizes and throughout a variety of article placements or sleeping positions. Further, such flattened configuration allows for the predictable flow of body exudate to the middle region 42, which exudate may drop or wick onto the flat-back, protection feature 30 while a wearer is sleeping.

The absorbent article 10 further includes in one embodiment, garment attachment patches 91, 92 on the garment-facing surface of the liquid impermeable backsheet 17. In one embodiment, two wing attachment patches 91 are present on the undersurfaces of the wings 15, and a main garment attachment patch is present along or about the central longitudinal axis Lc of the garment-facing surface of the liquid impermeable backsheet 17. Such attachment patches 91, 92 are used to help adhere the article to a wearer's undergarment when worn. Such attachment patches may be patches of adhesive, hook and loop fasteners, or a combination thereof, but desirably in one embodiment, are adhesive patches. Such patches are desirably each also covered by an adhesive-protective layer or release sheet 90, typically a coated film or coated paper sheet. As such adhesive, hook and loop fasteners, and release sheets are well known in the absorbent article art, they will not be described further. While not illustrated in the figures, additional adhesive patches may also be present along the widest part of the backsheet layer 17 garment-facing surface and towards the article back end 12, so as to help facilitate attachment of the article to the inside backside-facing surface of a wearer's undergarment.

The absorbent article 10 has in one embodiment, an overall length L1 of between about 280 and 420 mm, alternatively, between about 300 and 350 mm. The absorbent article 10 has in one embodiment, an overall width T1, of between about 90 and 180 mm, alternatively, between about 155 and 175 mm. In one embodiment, the length L2 of the flat-back, protection feature 30 is between about 120 and 180 mm, alternatively, between about 130 and 160 mm, still alternatively, between about 145 and 155 mm. In one embodiment, the flat-back, protection feature 30 extends from a position adjacent the middle region 42, to the back end 12. Alternatively, the feature may extend from a position adjacent the middle region 42 to a location short of the rearward edge of the back end 12 (not shown). Alternatively, the flat-back, protection feature may extend from the front end 11, to the back end 12, but only be elevated either entirely or substantially along the back region 43. In one embodiment, the width T2 of the flat-back, protection feature is between about 15 and 50 mm, alternatively, between about 20 and 30 mm, still alternatively, between about 22 and 24 mm. Such width is in one embodiment, narrower than the width of the underlying absorbent layer 18. In one embodiment, the width T2 of the flat-back, protection feature is uniform across its length L2. In a further alternative embodiment, the width T2, of the flat-back, protection feature is non-uniform along its length, such as being wider along its length at locations approaching the article back end 12, and such as those configurations illustrated in FIGS. 10A and 10B.

In one embodiment, the wider end of the flat-back protection feature, such as that wider end 155, 158 illustrated in FIGS. 10A and 10B, includes flared longitudinal side edge portions that flare outwardly towards the longitudinally-directed side edges 13, 14, of the absorbent article 10 or the back end 12. In such an embodiment, the wider, flared portions may include outwardly curved elastic material (not shown), such as sheet material, or a series of level elastic strands which curve towards the side edges 40. The depth D (or thickness) of the flat back, protection feature 30 is desirably in one embodiment, generally the same D across both the length and width of the feature. In an alternative embodiment, the thickness of the elastic portions (such as for example the thickness of the elastic, strand-containing portions including 36A, 36B, and 36C) of the flat-back, protection feature is the same across the width and length dimensions of the flat-back, protection feature. Such thickness may range in one embodiment from between about 0.1 and 1.5 mm, alternatively, between about 0.5 and 0.9 mm. In a further alternative embodiment, the flat-back, protection feature 30 is generally level across its width, such that there are no raised or peaked regions along its length (other than the sporadic gathers resulting from the contraction of non-elastic sheets on elastic materials of the feature). In one embodiment, the elastic material or materials are level across the transverse axis (width), such that if an imaginary line were to be drawn straight across the width (T axis) of the flat-back, protection feature 30 (and the line is either perpendicular to the longitudinal side edge 40 (in the case of parallel side edges) of the feature or the same distance from one longitudinal end to the other), the elastic material would be level across such imaginary line.

The front end directed fastening region 31 (between the two ends 31A and 31B) is in one embodiment, of a length L3 of between about 10 and 30 mm, alternatively, between about 20 and 25 mm. The back end directed fastening region 32 is in one embodiment, of a length L5 of between about 10 and 50 mm, alternatively, between about 35 and 40 mm. In one particular embodiment, the length of the back end directed fastening region L5 is the same as the length of the peripheral sealing region 60 (not shown). In one embodiment, the middle elevated flat-back protection region 33 has a length L4 (when in a relaxed contracted state) of between about 80 and 140 mm, alternatively, between about 95 and 110 mm. In one embodiment, the length L6 of the absorbent article front region 41 is between about 30 and 100 mm, alternatively between about 50 and 70 mm, the length L7 of the absorbent article middle region 42 is between about 80 and 170 mm, alternatively, between about 100 and 150 mm, and the length L8 of the absorbent article back region 43, is between about 125 and 225 mm, alternatively, between about 155 and 195 mm. In one embodiment, the length L9 of the spatial gap 27 between one embossment feature 24 and a longitudinally adjacent embossment feature 25, is between about 2 and 20 mm, alternatively between about 3 and 15 mm, still alternatively, between about 3 and 5 mm. The spatial gap 27 is the shortest distance formed between imaginary parallel lines which are drawn tangential to the end of the longitudinally adjacent embossment features 24, 25 as shown. In one embodiment, such spatial gap is entirely situated either beneath or laterally adjacent the elevated middle region 33 of the flat-back, protection feature 30. In one embodiment, only one of the longitudinally adjacent embossment features 25 includes portions 25A which extend laterally beyond the longitudinal side edges 40 of the flat-back, protection feature 30 when viewed from the top plan view. Alternatively, both longitudinally adjacent embossment features 24, 25 include embossment features which extend laterally beyond the longitudinal side edges 40, when viewed from the top plan view. In a further alternative embodiment, the entirety of the embossment feature 25 extends laterally beyond the longitudinal side edges, when viewed from the top plan view (not shown in FIG. 1, but shown in FIG. 12). In still a further alternative embodiment, all embossment features immediately adjacent the elevated portion 33 of the flat back, protection feature are positioned laterally outward from the longitudinal side edges 40 of the flat-back, protection feature (also as seen in FIG. 12).

A side perspective view of the absorbent article 10 with flat-back, protection feature 30 of FIG. 1, is illustrated in FIG. 2A. As can be seen in FIG. 2A, the flat-back, protection feature 30 includes at least along its elevated middle region 33 and along length L4, slight gathers or ruffles which result from the relaxed elastic materials in the flat-back, protection feature 30 gathering at least an attached inelastic layer along its length L4. The gathering creates the slight ridges across the feature between bond points on the elastic materials, but still the overall feature 30 remains substantially flat or level across its transverse direction (and along its entire length), such that no distinct peak or apex is formed by an individual elastic material along the entire feature length, and the elastic layer or strands remain generally level across the transverse axis of the feature (subject only to the irregular gathering). The contraction of the elastic features causes the back end 12 of the absorbent article 10 to curve upward such that the article ends 11, 12 are brought slightly closer together when the article is placed on a level surface. The unbent length L4 of the flat-back, protection feature 30, is shorter than the bent or curved length L10 of the adjacent base-pad structure 29. The length L4 can be extended under tension however, such that it approaches and in some instances is equal to, the length dimension of the underlying base-pad structure L10. It is desirable in one embodiment for the ratio of L4 (in open and unbent state on a flat surface): L10 to be about 1:1.2 (such as seen for example in FIG. 2A). The elastic material in FIGS. 1 and 2A causes the feature 30 to bias upwards in its relaxed position, thereby placing it in close association with a wearer's intergluteal cleft region during wear. As seen in FIG. 2A, the spaced apart embossment features 24, 25 are positioned vertically beneath the flat-back, protection feature 30. The flat-back, protection feature 30 is elevated above the wearer-facing surface of the liquid permeable topsheet layer 16, such that a space forms between the flat-back, protection feature 30 and the topsheet layer 16. The feature 30 may be positioned in the intergluteal cleft of a wearer and help maintain the article in position throughout an extended time frame, even though a wearer's undergarments (to which the article is fastened via patches 91, 92) may shift slightly during various sleeping positions. The relatively flattened, flat-back, protection feature 30 provides a comfortable fluid transfer feature for a wearer of the article, without an elevated, peak-like protuberance which could result in frictional irritation to sensitive areas of a wearer's anatomy. Body exudate which drops or wicks onto the flat-back, protection feature 30 may readily travel down the feature towards the central fluid deposition region of the article (middle region 42) to be absorbed into the article and stored until article disposal. Alternatively, the body exudate may seep through the material of the feature 30 and fall onto the topsheet layer 16 below (eventually to be absorbed by the absorbent layer 18).

It is desirable in one embodiment for the distance L5 to be greater than the distance L3, alternatively such that the ratio of L5 to L3 is about 1.7 to 1. It may be desirable to include a larger L5 so that there is more stability towards the back end of the article, where high stress may be commonplace. Further, by utilizing a relatively larger L5, the article can avoid back end curling, which is more likely with shorter fastening dimension. Such back end curling will lead to discomfort and the possibility that garment adhesive on the garment-facing surface of the backsheet layer 17, will inadvertently stick to the wearer's skin. In one embodiment, if an embossment across the central longitudinal axis is present, it desirably crosses the axis in the back region outside of the fastening region 32 (as seen in FIG. 1).

In an alternative embodiment of an absorbent article 101 in accordance with this disclosure, a flat-back, protection feature 102 (as seen in the side perspective view of FIG. 2B) may be formed from an either elastic or inelastic sheet (or sheets) having a relatively non-gathered appearance. If of an inelastic sheet material (such as an inelastic film or fibrous nonwoven sheet) the length L4 of the alternative flat-back, protection feature 102 would always be shorter than the underlying base-pad structure L10 such that it is always situated in the intergluteal cleft region of the wearer of the article and never extends under applied tension to match the length of the underlying base-pad structure L10 while in use. As with the previous embodiment of FIG. 2A, if formed of an elastic material, the flat-back, protection feature will in one embodiment have an extended length (upon application of pressure of a wearer upon the article) that is as long as the length L10 of the immediately subjacent base-pad, structure 29.

Figure 3:
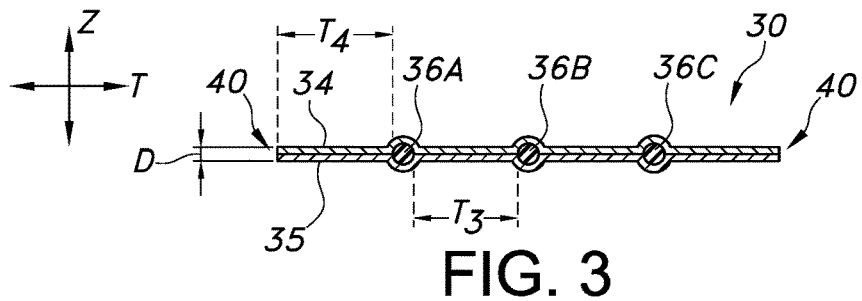
FIG. 3 illustrates a cross-sectional view of only the flat-back, protection feature of the absorbent article of FIG. 1, at lines 3-3 (the same appearance at both locations along the longitudinal axis of the absorbent article).

A cross-sectional view of only the flat-back, protection feature 30 of FIG. 1, is shown in FIG. 3. The view is for the flat-back, protection feature taken along lines 3-3 of FIG. 1 (two locations which have the same cross-sectional view). As can be seen in the Figure, in one embodiment, the flat-back, protection feature 30 may include a separate upper liquid permeable layer 34 and a lower liquid permeable layer 35 which bonded layers together envelope three individual elastic strands 36A, 36B, 36C. The elastic strands are at the same level across the transverse direction of the feature 30 (at all points along the length). The upper and lower layers 34, 35 are bonded (typically by adhesive bonding) to the elastic strands 36A, 36B, 36C while the strands are in an elongated configuration, such that after the elongated elastic strands are allowed to contract/relax (while the article is not being stretched to a flat condition), they form slight gathers along the length of the flat-back, protection feature 30. The upper and lower layers are not designed for absorbency, such that they readily assist the transfer of body exudate along the feature length to the middle region 42 of the article, for eventual deposition in the absorbent layer 18. In one embodiment, the upper and lower layers 34, 35 are formed from generally hydrophobic, fibrous nonwoven or film-based sheeting, which do not collect any appreciable amount of body exudate. Such flat-back, protection feature 30 further does not contain any hydrophilic absorbent material, such as cellulosic or superabsorbent-containing layers, or other internal hydrophilic layers.

In one embodiment, the spacing T3 between adjacent, and parallel elastic strands 36A, 36B, 36C of the flat-back, protection feature 30 (as measured from the closest side edge of one strand to that of an immediately adjacent strand) is between about 2 and 10 mm, alternatively, between about 3 and 5 mm. In one embodiment, the distance between adjacent strands is larger than 6 mm. In one embodiment, such parallel elastic strands are situated apart from the longitudinal side edges 40 of the flat-back, protection feature 30 such as by a distance T4 from the closest side edge of between about 4 and 15 mm, alternatively, between about 6 and 10 mm.

Figure 3A:
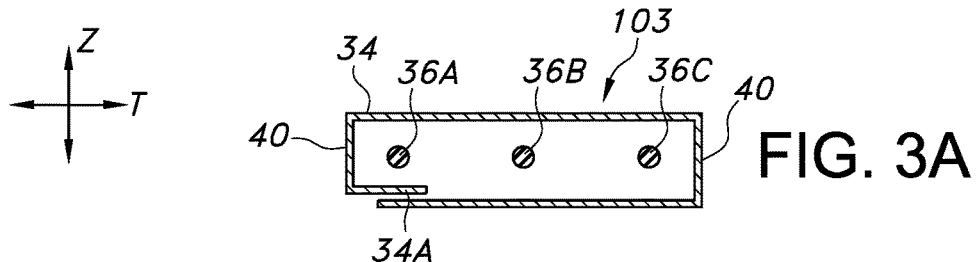
FIG. 3A illustrates an exploded, cross-sectional view of an alternative embodiment of only the flat-back, protection feature of the absorbent article of FIG. 1, at locations similar to those of FIG. 3.

An alternative embodiment of a flat-back, protection feature 103 is illustrated in an exploded cross-sectional view in FIG. 3A. Such cross-sectional view is taken at approximately the same location of an alternative absorbent article, as that location shown in FIG. 3. As seen in the alternative embodiment, a single sheet of liquid permeable material 34 envelops the three elastic strands 36A, 36B, and 36C and is attached along an undersurface seam by a bonding mechanism 34A. The undersurface seam is located closer to one side edge 40 than the other. Such bonding mechanism may be for example, a line of adhesive, a thermal, or ultrasonic bond, or a combination thereof, along the longitudinal axis of the flat-back, protection feature 103.

Figure 3B:
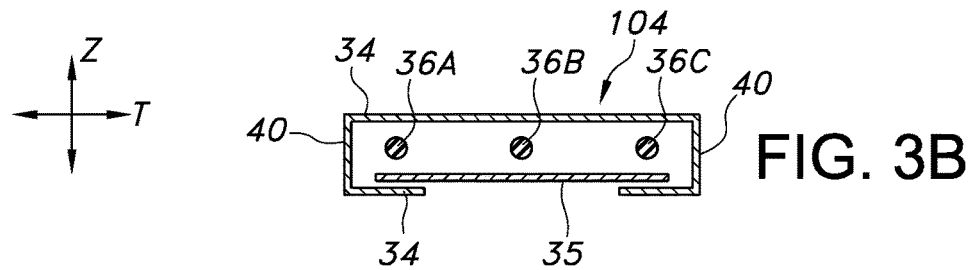
FIG. 3B illustrates an exploded, cross-sectional view of an alternative embodiment of only the flat-back, protection feature of the absorbent article of FIG. 1, at locations similar to those of FIG. 3.

A further alternative embodiment of a flat-back, protection feature 104 is illustrated in an exploded cross-sectional view in FIG. 3B. Such cross-sectional view is taken at approximately the same location of an alternative absorbent article, as that location shown in FIG. 3. As seen in the alternative embodiment, an upper liquid permeable sheet of material 34 envelops three elastic strands 36A, 36B, and 36C on three sides, and a lower liquid permeable sheet 35 is attached along two longitudinally directed seams to the upper liquid permeable sheet 34. The bonding mechanisms in this alternative embodiment may be for example, by adhesive, thermal, or ultrasonic bonds, or a combination thereof.

Figure 3C:
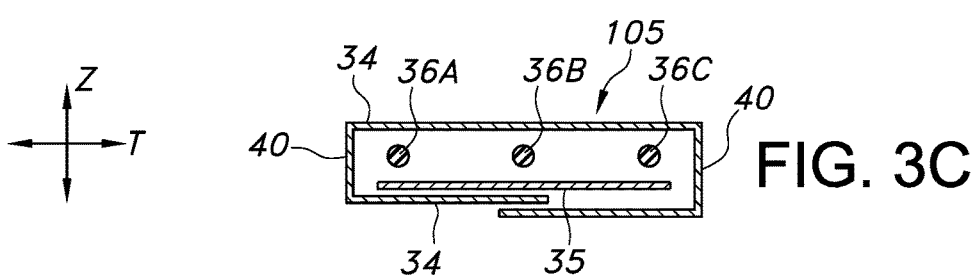
FIG. 3C illustrates an exploded, cross-sectional view of an alternative embodiment of only the flat-back, protection feature of the absorbent article of FIG. 1, at locations similar to those of FIG. 3.

In still a further alternative embodiment, a flat-back, protection feature 105 is illustrated in an exploded cross-sectional view in FIG. 3C. Such cross-sectional view is taken at approximately the same location of an alternative absorbent article as that shown in FIG. 3. As seen in the alternative embodiment, an upper sheet of liquid permeable material 34 envelops three elastic strands 36A, 36B, and 36C and is attached along a seam to a lower liquid permeable sheet 35, which is also enveloped by the upper liquid permeable sheet 34. The bonding mechanisms in this alternative embodiment may be for example, by adhesive, thermal, or ultrasonic bonds, or a combination thereof. In such embodiment, the upper liquid permeable sheet 34, which envelops both the elastic strands and the lower liquid permeable sheet 35 is bonded together along a seam that is positioned along the central longitudinal axis of the flat-back, protection feature 105 and the absorbent article (not shown).

It should be noted that the upper and/or lower layers 34, 35 may in a further alternative embodiment, be manufactured from a liquid impermeable material such that body exudate that makes contact with such flat-back, protection feature will more readily move along the feature top surface to an absorbent layer 18, rather than having to move through the pores of a liquid permeable layer along the feature to the absorbent layer 18. Of course, if both the upper and lower layers 34, 35 are both liquid permeable, body exudate can flow along the surface of the feature 105, or through the feature to a subjacent layer along the article length.

Figure 3D:
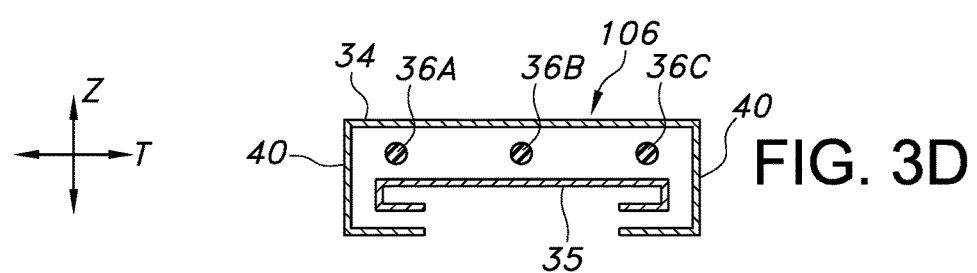
FIG. 3D illustrates an exploded, cross-sectional view of an alternative embodiment of only the flat-back, protection feature of the absorbent article of FIG. 1, at locations similar to those of FIG. 3.

In yet a further alternative embodiment, a flat-back, protection feature 106 is illustrated in an exploded cross-sectional view in FIG. 3D. Such cross-sectional view is taken at approximately the same location of an alternative absorbent article as that shown in FIG. 3. As seen in the alternative embodiment, an upper sheet of liquid permeable material 34 envelops three elastic strands 36A, 36B, and 36C, and partially an underlying liquid permeable layer 35. The upper layer 34 is attached along two underlying lateral seams to the lower liquid permeable sheet 35. The bonding mechanisms in this alternative embodiment may be for example, by adhesive, thermal, or ultrasonic bonds, or a combination thereof. The upper liquid permeable sheet 34 is folded partially about the lower liquid permeable sheet 35 with all lateral edges folded over such as to form the inverted "C" shaped configuration of the figure.

It should be recognized that while three, spaced apart elastic strands are illustrated in the preceding figures, alternative numbers of elastic strands, ribbons, or sheets (or combinations thereof) may alternatively be present in the flat-back, protection feature 30, as long as the elastic material(s) are maintained in a level configuration across the transverse axis (width) of the formed flat-back, protection features (for the feature entire length).

It should also be recognized that the flat-back, protection feature may be entirely liquid permeable as described above, or alternatively, partially liquid permeable, or may be entirely liquid impermeable. The term "liquid permeable" does not for the purposes of this disclosure, equate to the term hydrophilic. It shall however mean that liquid may flow through the described layer. The flat-back, protection feature may be breathable or non-breathable, and may alternatively, include mechanically formed apertures to allow for body exudate to more easily pass through its structure to subjacent layers.

Figure 4:
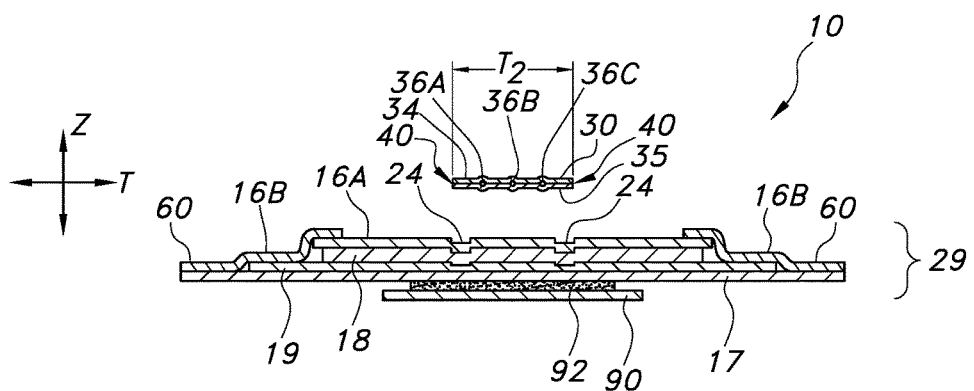
FIG. 4 illustrates a cross-sectional view of the entire absorbent article of FIG. 1 (flat-back, protection feature and base-pad, structure), at line 4-4.

A cross-sectional view of the absorbent article 10 of FIG. 1, is shown in FIG. 4. Such cross-sectional view illustrates along line 4-4 of FIG. 1, that the flat-back, protection feature 30 is generally flat across the transverse axis T at all locations along the length of the feature, and that each of the elastic features 36A, 36B, 36C (if present in multiple numbers) are level across the feature length.

The garment fastening mechanism 92 (i.e. adhesive) is particularly seen along the backsheet layer 17 underlying surface, and is covered by a release sheet or paper 90. The flat-back, protection feature is shown in an elevated orientation above the topsheet layer 16, and in particular above the central topsheet layer 16A of the base-pad structure 29.

Figure 5:
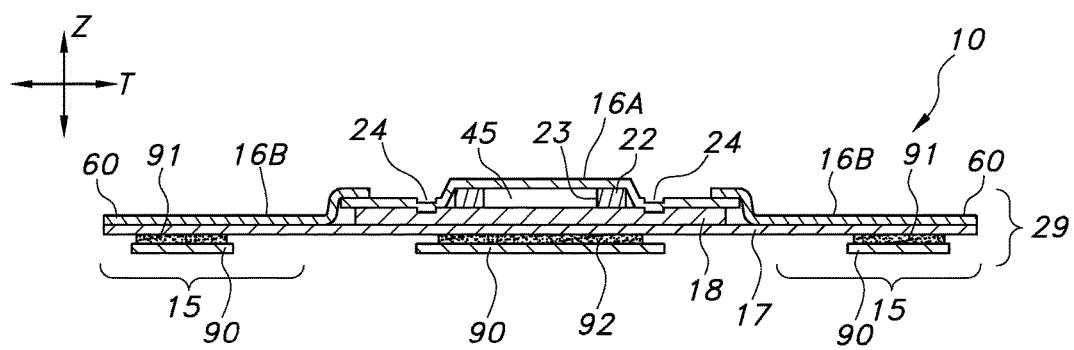
FIG. 5 illustrates a cross-sectional view of the entire absorbent article of FIG. 1, at line 5-5.

A cross-sectional view of the absorbent article 10 of FIG. 1, is also shown in FIG. 5. Such cross-sectional view illustrates along line 5-5 of FIG. 1, that the flat-back, protection feature 30 is in one embodiment, absent from the base-pad structure 29 in the article middle region 42. In this fashion, there is no flat-back, protection feature in the middle region 42 to interfere with the flow of body exudate along the article depth direction Z. Body exudate that is deposited in this region either directly, or by wicking along the flat-back, protection feature 30, may flow directly from the topsheet layer 16A into the annular opening 45 and eventually to the absorbent layer 18. Body exudate may collect in the annular opening 45 (defined by the oval edge 23 of the transfer layer 22), or may be rapidly absorbed into the absorbent layer 18. The garment fastening mechanisms 91, 92 (i.e. adhesive) are particularly seen along the backsheet layer 17 garment-facing surface, and on the garment-facing surface of the wings 15. Each fastening mechanism is covered by release paper 90.

Figure 6A:
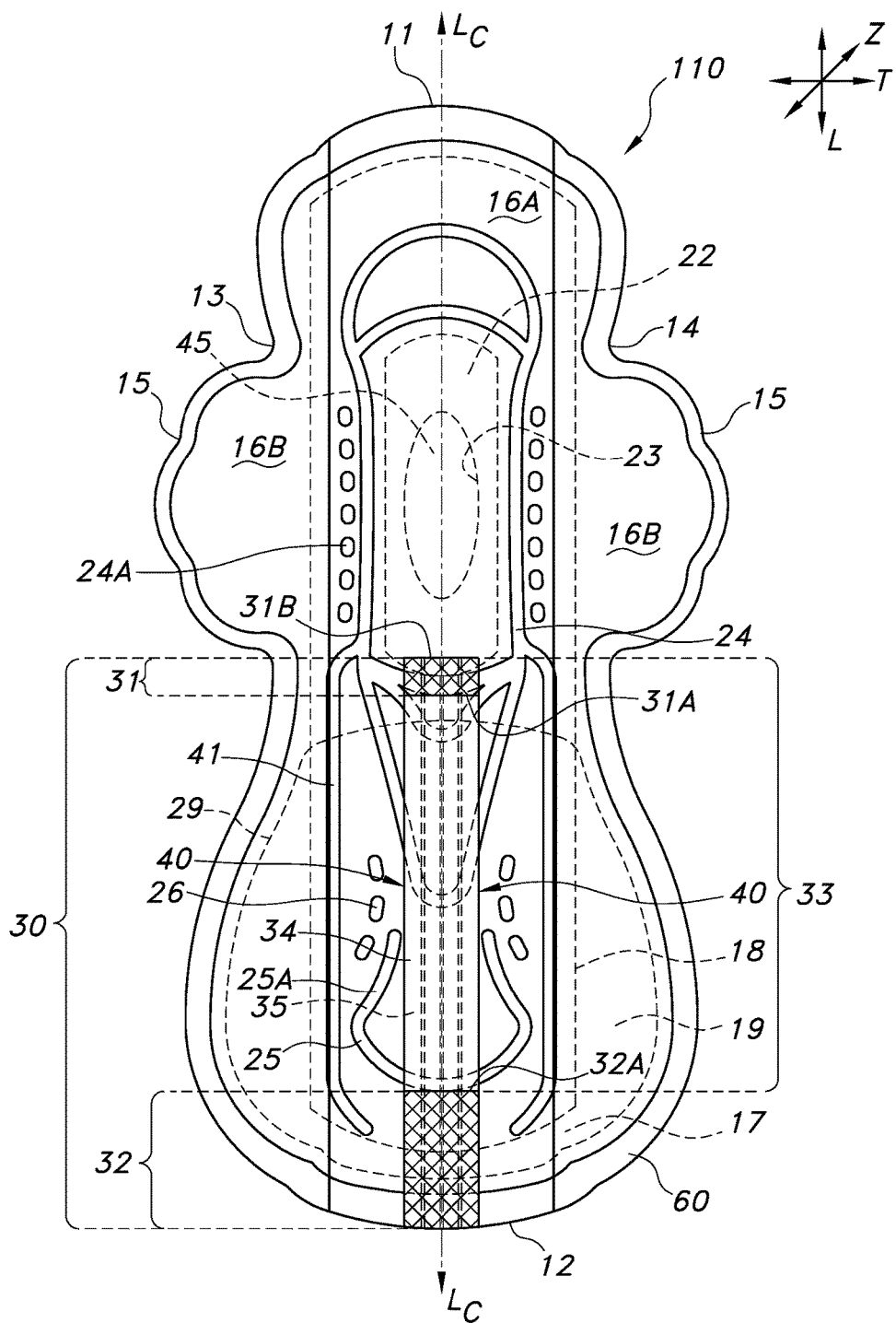
FIG. 6A illustrates a top plan view of an alternative embodiment of an absorbent article having a flat-back, protection feature shown with the article in an open and relaxed position, shown with the article in an open and uncontracted position.

A top plan view of an alternative embodiment of an absorbent article 110 with flat-back, protection feature 30 is illustrated in FIG. 6A. As seen in the figure, in addition to having a pair of longitudinally spaced-apart embossing features 24, 25 in the base-pad structure 29, an additional encircling embossing feature 41 may be positioned laterally beyond the spaced-apart embossing features 24, 25, and embossing feature 26. Such additional encircling embossing feature may provide an outermost barrier outward from the flat-back, protection feature 30 in the back region.

Figure 6B:
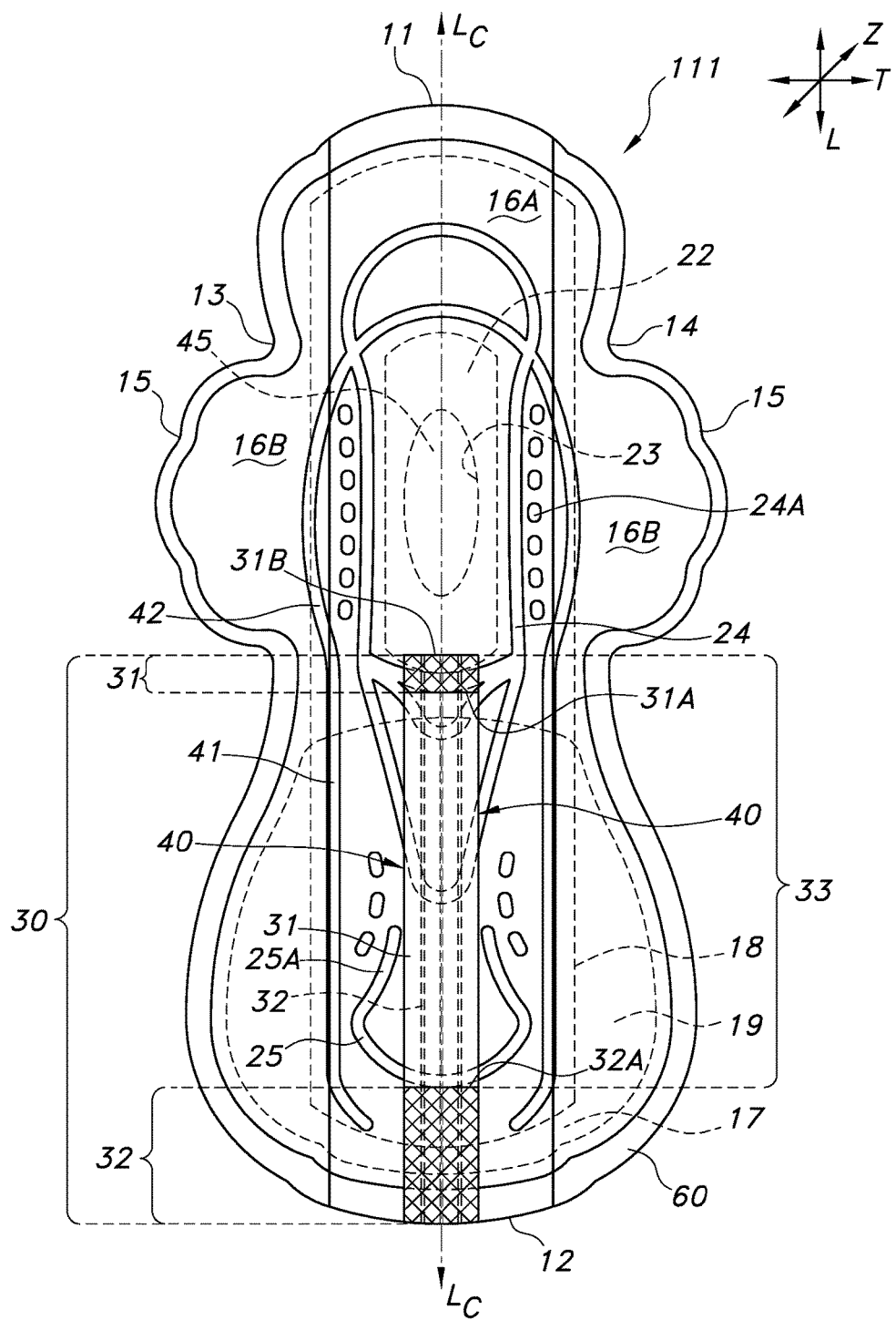
FIG. 6B illustrates a top plan view of still a further alternative embodiment of an absorbent article having a flat-back, protection feature, shown with the article in an open and uncontracted position.

A top plan view of a further alternative embodiment of an absorbent article 111 with flat-back, protection feature 30 is illustrated in FIG. 6B. As seen in FIG. 6B, in addition to having a pair of longitudinally spaced-apart embossing features 24, 25 in the base-pad structure 29, additional encircling embossing features 41, 42 may be positioned laterally beyond the spaced-apart embossing features 24, 25, and embossing feature 26, in the middle and back regions. Such additional encircling embossing features 41, 42 may provide an outermost barrier outward from the central fluid deposition region and the flat-back, protection feature 30.

As seen in FIG. 7, in yet another alternative embodiment of an absorbent article 120 with a flat-back, protection feature 30A, such feature 30A may include an extended length portion 37 which is bonded to the base-pad structure 29 towards the front end 11 of the absorbent article 120 along a lengthy bond area 38. Such extended length portion 37 has a length L 11 in one embodiment of between about 140 and 240 mm, alternatively, between about 170 and 190 mm. Such extended length portion 37 is in one embodiment, bonded to the topsheet layer 16 (or 16A as the case may be) such that it cannot elevate above the base-pad structure 29 in the middle 42 and front 41 regions of the absorbent article 120. Such lengthy bond area 38 is an extension of the front end directed fastening region and does not allow for elastic functionality in the middle 42 and front 41 regions of the absorbent article 120, as the elastic materials 36A, 36B, 36C (if present) are tacked down and not capable of significant contraction within the article 120. In such embodiment, the flat-back, protection feature 30A is bonded to the base-pad structure across the peripheral seal region 60. In yet another alternative embodiment, as also illustrated in FIG. 7, discrete and differentiated portions of the absorbent layer 18A, 18B (or either of the layers 18, 19) are positioned about the central longitudinal axis Lc of the absorbent article 120. Such differentiated absorbent layer portions may include either lower or higher basis weights or densities of absorbent material. Such differentiated absorbent layer portions are in one embodiment, located laterally beyond the longitudinal side edges 40 of the elevated portion of the flat-back, protection feature 33, such that they improve shaping of the article (pad) in the back region 43. Such differentiated absorbent layer portions may also be used to visually highlight the presence of the flat-back protection feature. They may be formed by compression of the absorbent layer(s) in these regions. They may be colored or printed differently from surrounding absorbent layer regions.

Figure 8:
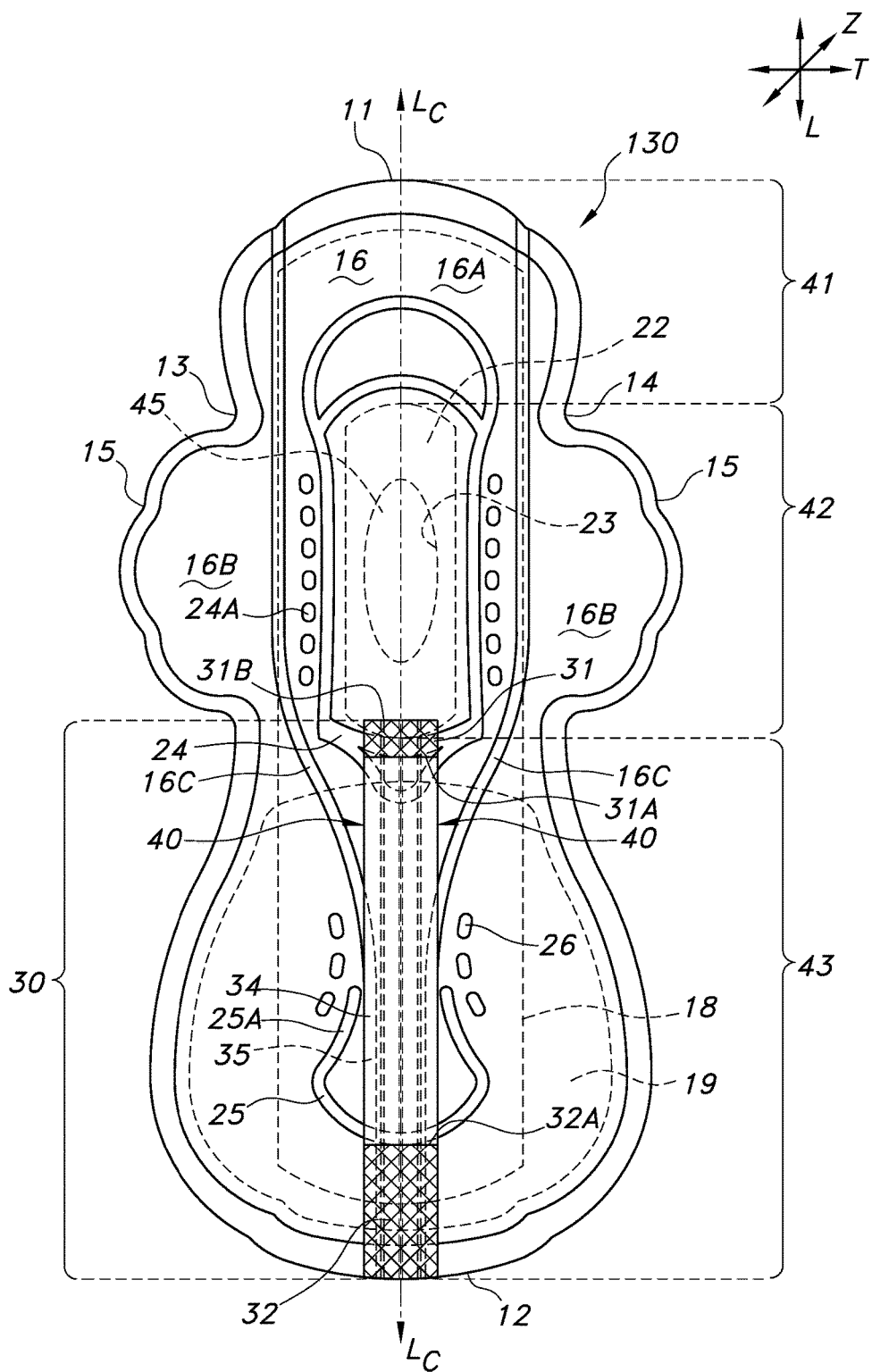
FIG. 8 illustrates a top plan view of still a further alternative embodiment of an absorbent article having a flat-back, protection feature, shown with the article in an open and uncontracted position.

In still a further alternative embodiment of the absorbent article 130, as seen in FIG. 8, the opposing side topsheet layers 16B of a dual cover topsheet layer 16 (including a central topsheet layer 16A and opposing side topsheet layers 16B), may each include a proximal edge 16C which extends along a path on the longitudinal axis of the absorbent article 130 which takes it under the flat-back, protection feature 30 towards the back region 43 of the article, and is proximal to the central longitudinal axis Lc. Such proximal edges 16C are placed further apart from the central longitudinal axis at locations adjacent the front region 41 of the absorbent article 130. The proximal edges 16C may either lie flat against the central topsheet layer 16A, or alternatively may be elevated either based on an unbonded portion of the opposing side topsheet layers 16B adjacent the proximal edge, or alternatively, based on the inclusion of an elastic element (not shown) that is under tension and attached to, or adjacent the proximal edges 16C, which unbonded or elastic features cause the proximal edges 16C to rise above the surface of the underlying layers when the article is in use. In an alternative embodiment, such proximal edges 16C, may themselves form an elevated flat-back protection feature defining an elongated planar structure, without the need for a separate layer.

Figure 9:
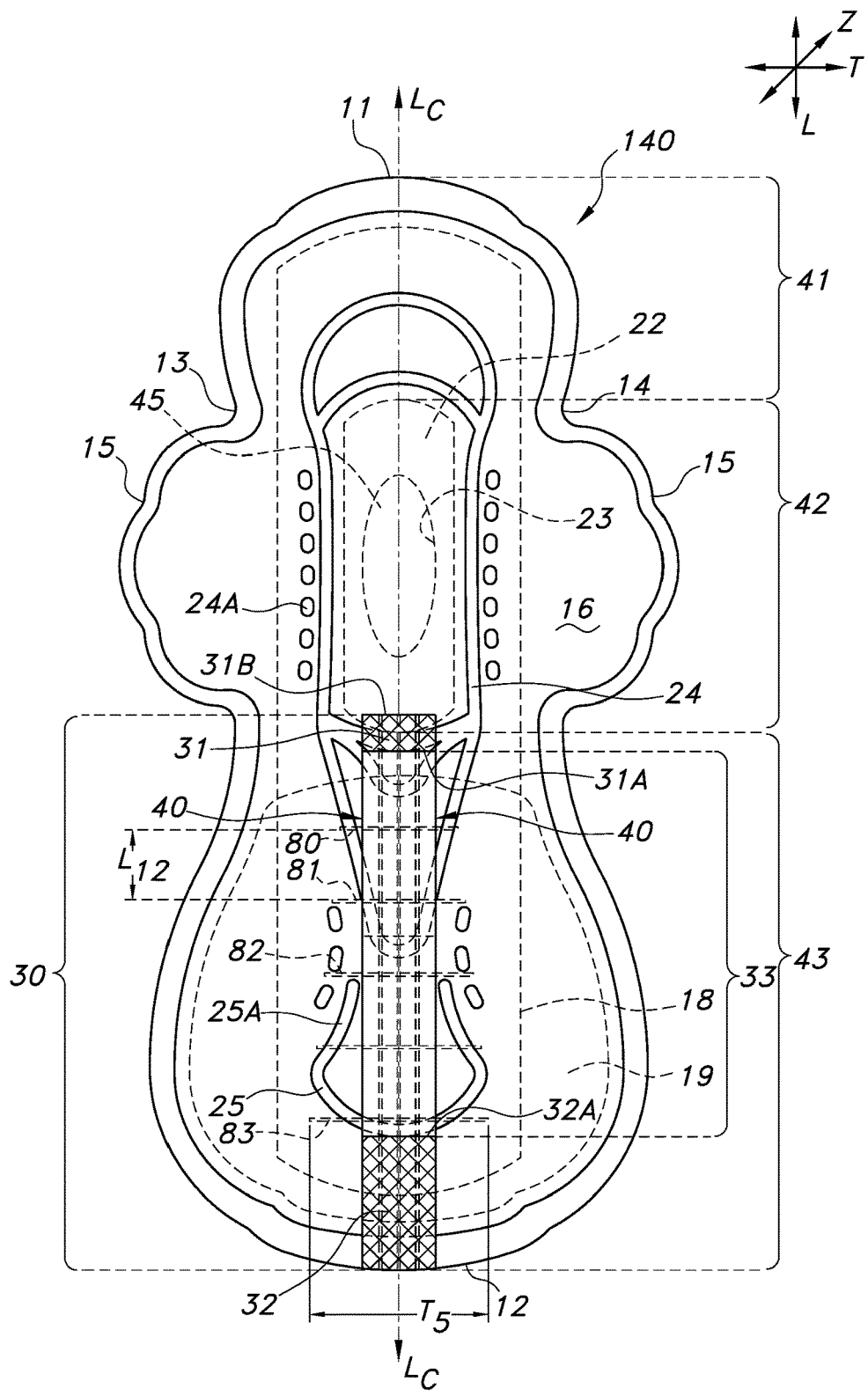
FIG. 9 illustrates a top plan view of still a further alternative embodiment of an absorbent article having a flat-back, protection feature, shown with the article in an open and uncontracted position.

In still another alternative embodiment of the absorbent article 140, as seen in FIG. 9, the absorbent article 140 with flat-back, protection feature 30 includes within one or more of the absorbent layers 18, 19 lines of weakness 80, 81, 82, 83 spaced apart along the central longitudinal axis of the article. The lines of weakness are in one embodiment, all located beneath the elevated region 33 of the flat-back, protection feature 30, when viewed from the top plan view. The lines of weakness may extend laterally beyond the longitudinal side edges 40 of the flat-back, protection feature 30, but need not. In one embodiment, the lines of weakness each have a width dimension T5 along the article transverse axis of between about 20 and 70 mm, alternatively between about 30 and 60 mm. In one alternative embodiment as shown, the lines of weakness may include progressively wider dimensions along the transverse axis, as they are positioned closer to the back end 12 of the absorbent article 140. For example, the width of line 80 will be shorter than that of line 81. The width of line 81, may be shorter than that of line 82 and so forth. The lines of weakness may be created by numerous techniques, such as for example by slitting, perforation, aperturing, or by other mechanisms for separating, reducing, or eliminating absorbent layer material in those areas. Such lines of weakness may be continuous as shown, or alternatively, may be formed from a series of discontinuous holes, slits, or dash shaped regions. The lines of weakness 80, 81, 82, 83 are designed to impart greater flexibility in the absorbent article back region 43 beneath the elevated portion 33 of the flat-back, protection feature 30. The lines of weakness are in one embodiment, spaced apart of each other along the longitudinal axis by a distance L 12 of between about 5 and 25 mm, alternatively, between about 10 and 15 mm. In an alternative embodiment, the lines of weakness 80, 81, 82, 83 are present in all absorbent layers located in the back region 43 of the absorbent article 140.

In another alternative embodiment of an absorbent article 150 with a flat-back, protection feature 151 as seen in the top plan view of FIG. 10A, the absorbent article 150 includes along the length of the flat-back, protection feature 151, a wider region 152 which width increases as it approaches the back end 12 of the absorbent article. The width of the flat-back, protection feature 151 may increase gradually or rapidly. In one embodiment, the width increases in the elevated region 153 that is not directly bonded to the base-pad structure 29. In one particular embodiment, the flat-back, protection feature 151 includes an outwardly flared portion 154 along each of its longitudinal side edges 40, that is flared outwardly from the central longitudinal axis Lc, and which flaring continues between the elevated region 153 and the bonded region 155 of the flat-back, protection feature 151. However, even though the feature 151 includes an outwardly flared portion towards the article back end 12, the flat-back, protection feature 151 remains flat across the transverse direction, in that the elastic components 36A, 36B, 36C are each level with one another along the longitudinal axis of the flat-back, protection feature 151. This flattened configuration can be seen in the cross-sectional view of FIG. 11 which shows the flat-back, protection feature 151 and base-pad structure 29 of the absorbent article 150 taken along line 11-11 of FIG. 10A. This particular embodiment includes a single topsheet layer 16, a single absorbent layer 18, and a backsheet layer 17. The elevated portion of the flat-back, protection feature 151 extends between the lines of attachment 155A and 31A on the fastening regions 155 and 31.

A top plan view of an alternative embodiment of an absorbent article 156 having a flat-back, protection feature 157 with a wider portion 158 located towards the article back end 12, is also illustrated in FIG. 10B. As seen in this alternative embodiment, an additional set of embossment features 28A are positioned on the base pad structure, symmetrically about the central longitudinal axis Lc, and also laterally outward from the longitudinal side edges 40 of the flat-back, protection feature 157, when viewed in the top view. This additional set of symmetrical embossment features 28A provide additional article shaping benefits to the absorbent article 156 adjacent the article back end 12, and particularly along the flared side edges 40 of the flared flat-back protection feature 157. In one embodiment, the additional set of embossment features 28A are positioned in a spaced relationship from the embossment feature 25, such that a spatial gap, either laterally, longitudinally or a combination thereof exists between the embossment features 25, 28A. In one embodiment, the additional embossment features 28A include outwardly flared portions which are aligned with the flare in the longitudinally directed side edges of the flat-back, protection feature 157. The absorbent article 156 of FIG. 10B may also in an alternative embodiment, include embossment features 28B on the flared portion of the flat-back, protection feature that is fastened 158 to the base-pad structure 29. Such embossment features 28B may be outwardly flared embossment features positioned in the back end directed fastening zone 158 (which is also flared). In one embodiment, the flare of the embossment features 28B is aligned with the flare of the longitudinal side edges 40 of the flat-back, protection feature 157. Such outwardly flared embossment features 28B also provide additional article shaping functionality and stability to the article 156 and flat-back, protection feature 157 respectively. Such embossments provide needed strength to the flared portion of the flat-back protection feature 157. It is desirable in one embodiment, for the embossment features (such as in FIG. 10B, the outwardly flared embossment features 28B), to be positioned off of the elastic strand component(s) 36A, 36B, 36C if such are present. Alternatively, such embossment features may not be flared, or may be positioned either on or off of the elastic features in the fastened regions of the flat-back, protection feature 157. It should be noted that while cross-hatching is not illustrated in the embodiment of FIG. 10B in order to more clearly show the fastened regions of the flat-back, protection feature, and associated embossment features 28B, such areas are fastened at these locations to the base-pad structure 29 as with previously described embodiments. The elevated portion of the flat-back protection feature 157 extends between the lines of attachment at 158A and 31A (of the fastening regions 158, 31).

In an alternative embodiment, discrete embossment options are further illustrated for example in FIG. 12, which shows a top plan view of still another embodiment of an absorbent article 160, having a flat-back, protection feature 30. In the embodiment of FIG. 12, a first series of discrete embossment features 53 is positioned in the front end directed fastening region 31, and inside from the front end directed fastening region edge 31A. The three discrete embossment features 53 include two angled, dash-like embossment features 53A and 53C, which are symmetrically placed about the central longitudinal axis Lc of the absorbent article. A single dash-like embossment feature 53B is placed along the central longitudinal axis Lc of the absorbent article 160. The three discrete embossment features 53 are spaced apart from a front end directed embossment feature 24C, such that a spatial gap defined by length L13 separates them. In one embodiment, the spatial gap L13 is between about 2 and 10 mm, alternatively, between about 4 and 7 mm. The spatial gap may be measured between the two closest edges of the front end directed embossment feature 24C and a discrete embossment feature 53. A further series of dash-like embossment features 54 are positioned towards the back end 12 of the absorbent article 160. The dash-like embossment features 54 also include a pair of outwardly angled embossment features 54A, 54C that are symmetrically about the central longitudinal axis Lc, and a single dash-like embossment feature 54B, which is positioned on the central longitudinal axis Lc. The dash-like embossment features 54, are positioned in the back-end directed fastening region 32, inward from the back-end fastening region edge 32A. The elevated portion of the flat-back protection feature 30 extends between lines 32A and 31A. The dash-like embossment features 54 are desirably separated from embossment feature 55 along the article longitudinal axis L, by a spatial gap defined by distance L14. In one embodiment, the spatial gap L14 is between about 3 and 15 mm, alternatively, between about 5 and 10 mm.

The embodiment illustrated in FIG. 12, also includes longitudinally separated embossment features 24B, and 55. The embossment feature 55, which is situated along the back region of the absorbent article, includes a slightly, outwardly flared portion 55A. It should be recognized from the figure, that the pattern of embossments of FIG. 12 are specifically placed on the absorbent article 160 so as to avoid interference with the functionality of the flat-back protection feature 30. Such embossments are either 1) located entirely lateral to the flat-back, protection feature, 2) separated along the longitudinal direction at a location adjacent to the flat-back protection feature 30, 3) cross the central longitudinal axis Lc only along parts of the base-pad structure 29 which do not include the flat-back protection feature 30 or where the flat-back protection feature 30 is actually fastened to the base-pad structure 31, 32. In such a manner, the embossing step of the absorbent article manufacturing process may be accomplished after the entire article is constructed (including the flat-back protection feature 30), without negatively impacting the ability of the flat-back protection feature 30 to elevate along the wearer's intergluteal cleft during use.

Furthermore, the intentional separation of longitudinally directed embossment features, such as the spaced-apart embossment features 53 and 24C, or the spaced-apart embossment features 54 and 55, provide for improved ability of the absorbent article to be folded prior to use. For example, a set of suggested absorbent article fold-lines are illustrated in FIG. 12. In particular, a first fold line 50 may be situated towards the back end 12 of the absorbent article 160. A more preferred fold line 51B is situated between spaced apart embossment features 24B and 55. In particular, such fold line 51B extends across the absorbent article 160 such that it does not cross any embossment feature. In the illustration, it passes between spaces of the embossment feature 26 (in spatial gap 27), and also between embossment feature 24B and 55. A further fold-line 51A is situated across the middle of the absorbent article 160 adjacent the wings 15, but not crossing the wings 15. Such middle fold-line is specifically placed between the discrete embossment features 53 and the embossment feature 24C. It crosses the absorbent article 160 along the front-end directed fastening region 31. An additional fold-line 52 is positioned towards the front end 11 of the absorbent article 160. The absorbent article 160 may include several of the described fold lines, such as for instance either fold-line 50 or 51B, fold-line 51A, and fold-line 52. Alternatively, such absorbent article 160 may only include fold-line 51A. By strategically placing the embossment features in locations along the length of the absorbent article 160 with flat-back protection feature 30, the article may be manufactured with relative ease, and in such a manner that the performance of the flat-back protection feature 30 is enhanced. The use of embossment features which cross the central longitudinal axis of the absorbent article in the fastening regions 31, 32, strengthens the flat-back protection feature 30 as well as the bonding which holds the feature to the base-pad structure 29.

As seen in FIG. 12, the end of the front fastening region 31B is positioned over the peripheral edge of the transfer layer 22. This need not be the case. In an alternative, the end 31B may instead be positioned over embossment feature 24C, or alternatively over embossment features 53A,B,C. In such a fashion, the embossment features (either 24C or 53A,B,C) may act to further strengthen the bond (such as the adhesive bond) of the fastening region 31, and also to hold down the end 31B. Such may also present a more finished appearance to the wearer of such article.

The gaps between adjacent embossment features seen in FIG. 12, such as between 24C and 53A,B,C add additional support for the article to cleanly fold for storage, and be unfolded prior to use. Such folding of the ends between embossment feature, over the wearer-facing surface of the topsheet layer 16, preserves the functionality of any elastic material in the flat-back protection feature prior to use.

Figure 13:
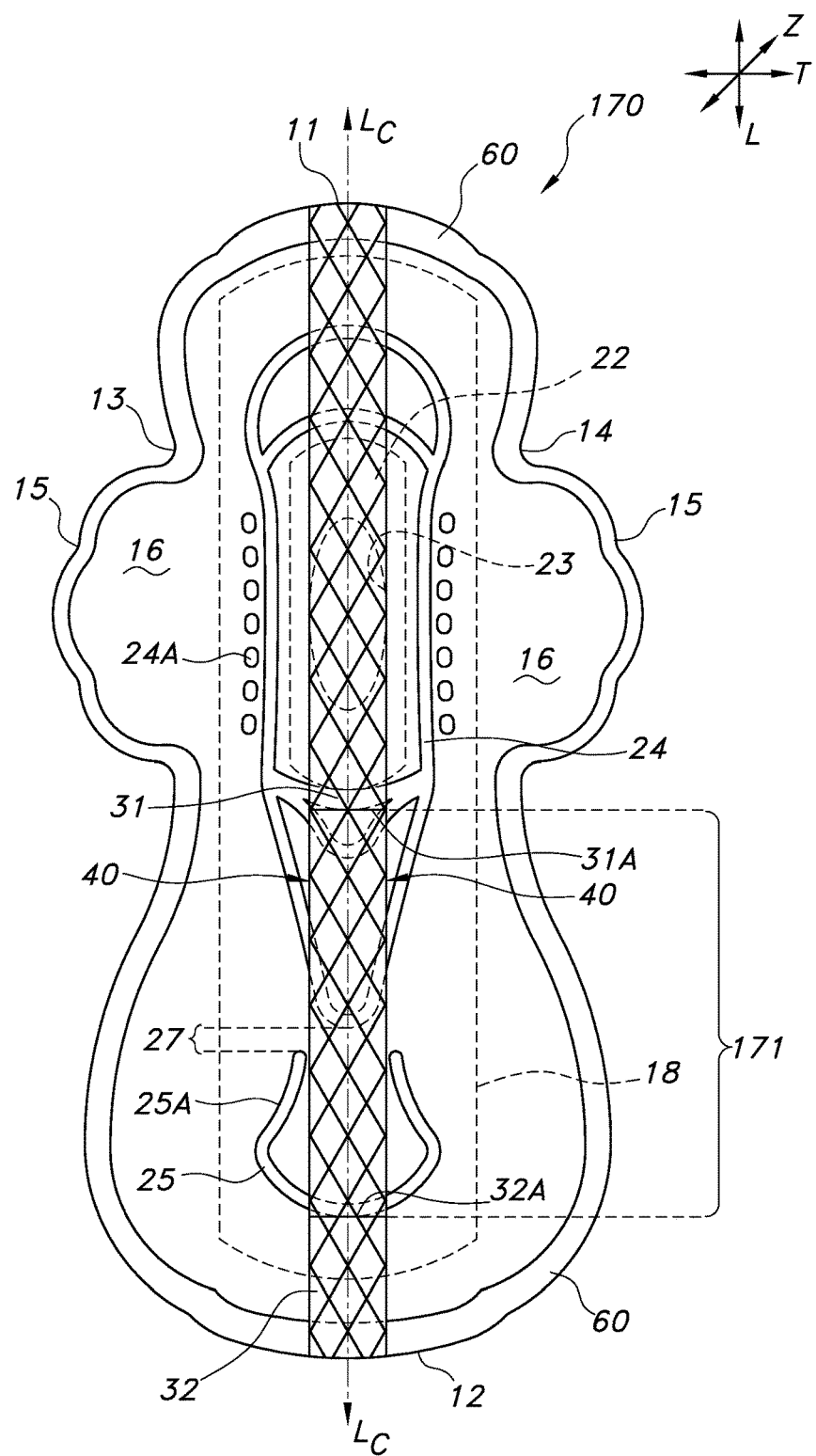
FIG. 13 illustrates a cross-sectional view of still a further alternative embodiment of an absorbent article having a flat-back, protection feature, shown with the article in an open and uncontracted position.

In yet another alternative embodiment of the absorbent article of the disclosure, a top plan view of an absorbent article 170 with flat-back protection feature 171 is illustrated in FIG. 13. As seen in the figure, a textured flat-back protection feature 171 extends along the central longitudinal axis Lc of the absorbent article 170. The flat-back protection feature 171 includes a textured or cushioned surface along its entire length, which is illustrated by the diamond pattern. Such textured surface may be either on an elongated planar structure that is shorter in length than the underlying base structure, or on an elastic sheet material, and may be provided by a laminated nonwoven sheet that has been laminated to the elastic sheet material at discrete points, such that the elastic sheet material may not be hindered from stretching along the article length L. In one embodiment, such flat-back protection feature 170 may include a relatively high transverse axis stiffness, such that it maintains its relatively level configuration between its longitudinal side edges and across its full width (transverse) direction.

As noted, the flat-back protection feature 30 desirably includes an elastic material such as elastic material formed from elastic strands that have been laminated between two opposing nonwoven webs, when the elastic strands are bonded to the webs while the strands are in a stretched condition. Alternatively, such flat-back protection feature is formed from a stretch-bonded laminate material. In any event, such feature should be capable of extending and retracting at least along the article longitudinal direction. In one embodiment, the elastic material(s) in the flat-back protection feature is capable of extending between about 105 and 145% during use and demonstrating a tension of between about 110 and 125%. In a further alternative embodiment, the elastic material or materials should have a uniform tension across the flat-back protection feature. For example, if the feature includes multiple stranded elastic material across the feature, each of the strands should have uniform tension. If the feature includes sheet elastic material, the sheet material should include uniform tension across the feature transverse direction.

In one embodiment, the transverse direction width of the fastening regions (31, 32) is larger than the transverse direction width of the elevated portion (non-fastened portion 33) of the flat-back protection feature. In still another alternative embodiment, at least one of the fastening regions (31, 32) include a transverse direction width that is larger than that of the elevated portion (non-fastened portion 33).

The liquid permeable topsheet layer 16 of the base-structure (or base-pad structure 29) may be manufactured from any number of conventional materials commonly used as a wearer-facing surface on an absorbent article. For example, non-limiting examples of such topsheet layer materials include fibrous nonwoven sheet materials, such as spunbond, spunlace, meltblown, and carded web materials (such as thermally bonded carded webs (TBCW), through-air bonded carded webs (TABCW)), fibrous woven sheet materials, apertured polyolefinic film or apertured fibrous nonwoven materials (single and dual apertured), and laminate combinations of the foregoing materials. Further, monolayered or multilayered sheet materials of the foregoing can also be used as the liquid permeable topsheet layer 16. Particularly, carded web materials may be made from staple, bicomponent fibers as are known in the art. Materials that may be used in the topsheet layer 16 include synthetic fibers, such as polyolefinic materials. Such topsheet layers 16 may themselves be embossed. Suitable topsheet layer materials include, but are not limited to those described in U.S. Pat. No. 4,397,644 to Matthews et al., U.S. Pat. No. 4,629,643 to Curro et al., U.S. Pat. No. 5,188,625 Van Iten et al., U.S. Pat. No. 5,382,400 to Pike et al., U.S. Pat. No. 5,533,991 to Kirby et al., U.S. Pat. No. 6,410,823 to Daley et al., and United States Publication 2012/0289917 to Abuto et al., each of which is hereby incorporated by reference thereto in its entirety to the extent not inconsistent with this disclosure.

As noted, the liquid permeable topsheet layer 16 may be a two layer (such as in the same or two different horizontal planes) or multi-component material with a central, longitudinally directed section positioned along and straddling the central longitudinal axis of the absorbent article, with lateral side-topsheet sections flanking and joined to each side (or side longitudinal edge) of the central longitudinally directed topsheet layer section. The central topsheet section may be made for example, from the aforementioned TABCW materials or it may be made from a perforated film that has been treated to be hydrophilic. The lateral side topsheet sections may be made from a different fibrous nonwoven material which is joined to the central longitudinally directed section, such as by adhesive or thermal bonding. Such a two layer topsheet configuration is described for example, in U.S. Pat. No. 5,961,505 to Coe, U.S. Pat. No. 5,415,640 to Kirby, and U.S. Pat. No. 6,117,523 to Sugahara, each of which is hereby incorporated by reference thereto in its entirety to the extent not inconsistent with this disclosure. It is also contemplated that such two layer topsheet materials may additionally include longitudinally extending elastic strand components (not shown) along their side edges to lift up components of the side-topsheet materials during use, thereby forming additional physical barriers or cupping features on the article so as to allow a fit more closely aligned to the body of a wearer. The liquid permeable topsheet layer 16 of the base-structure may also be treated so as to impart other properties to the wearer-facing surface. Examples of additional treatments include application of skin health agents, coloring agents, odor control agents, stain masking agents and the like.

The basis weight of nonwoven webs to be used as liquid permeable topsheet layers 16 of the base-structure may generally vary, such as from about 5 grams per square meter ("gsm") to 150 gsm, in some embodiments from about 10 gsm to about 125 gsm, and in some embodiments, from about 15 gsm to about 120 gsm. Desirably in one embodiment, the liquid permeable topsheet layer 16 of the base structure is a nonwoven material, such as a TABCW, spunbond or TBCW having a basis weight of between about 15 and 25 gsm, alternatively a 24 gsm hydrophobic TABCW material.

Optionally, one or more fluid transfer, surge, or distribution layers may be attached to the garment-facing surface of the liquid permeable topsheet layer 16 of the base-structure 29. Such additional layers include, but are not limited to, airlaid materials, bonded carded webs, hydroentangled nonwoven webs, spunbond webs, foam structures, and apertured films. Such optional layers may assist in directing body exudate to particular locations in the absorbent article, alternatively in spreading body exudate to various regions of an underlying absorbent layer, or alternatively, altering the speed by which body exudate moves through the absorbent article.

The one or more absorbent layers 18, 19 can each comprise a single layer or multiple layers and these one or more layers can themselves comprise similar or different materials, although a single layer of homogenous composition material is desirable in one embodiment. Highly absorbent core layers often include, but are not limited to, hydrophilic batts or webs containing wood pulp fibers, superabsorbent particles or fibers (known as SAP or SAM), synthetic wood pulp fibers, synthetic fibers, coform materials, hydrophilic foam materials, and combinations thereof. The absorbent core layer 18 may comprise any one of a number of materials and structures, the particular selection of which will vary with the desired loading capacity, flexibility, body fluid to be absorbed and other factors known to those skilled in the art. By way of example, suitable materials and/or structures for the absorbent core layers include, but are not limited to, those described in U.S. Pat. No. 4,610,678 to Weisman et al., U.S. Pat. No. 6,060,636 to Yahiaoui et al., U.S. Pat. No. 6,610,903 to Latimer et al., U.S. Pat. No. 7,358,282 to Krueger et al., and United States Patent Publication 2010/0174260 to Di Luccio et al., each of which is hereby incorporated by reference thereto in its entirety, to the extent not inconsistent with this disclosure.

The shape of the absorbent core layers 18, 19 (while generally shown as an oblong configuration to generally mimic the outer peripheral shape of the absorbent article 10, can vary as desired and can comprise any one of various shapes including, but not limited to, generally triangular, rectangular, dog-bone and elliptical shapes. In one embodiment, the absorbent core layer 18 has a shape that generally corresponds with the overall peripheral shape of the absorbent article 10 such that the absorbent core layer 18 terminates proximate the peripheral seal region 60. The dimensions of the absorbent core layer 18 can be substantially similar to those of the absorbent article 10, however it will be appreciated that the dimensions of the absorbent core layer 18 while similar, will often be slightly less than those of the overall absorbent article 10 in order to be adequately contained therein, and desirably sealed around the edges. Desirably in one embodiment, the absorbent core layer 18, 19 is either a fluff layer, airlaid layer, or compressed felt layer.

As noted, the individual layers comprising the absorbent article can be attached to one another using means known in the art such as adhesive, heat/pressure bonding, ultrasonic bonding and other suitable mechanical attachments. Commercially available construction adhesives usable in the present disclosure include, for example Rextac adhesives available from Huntsman Polymers of Houston, Tex., as well as adhesives available from Bostik Findley, Inc., of Wauwatosa, Wis.

The liquid impermeable backsheet layer 17 of the base-structure 29 functions to isolate absorbed fluids from the wearer's garments or bedding, and therefore desirably can comprise a variety of liquid-impervious materials. In one aspect, the liquid impermeable backsheet layer 17 may optionally comprise a material that prevents the passage of liquids but allows air and water-vapor to pass there-through. The liquid impermeable backsheet layer 17 can comprise a single layer or multiple layers, and these one or more layers can themselves comprise similar or different materials. Suitable liquid impermeable backsheet layer 17 materials include, but are not limited to, polyolefin films, nonwovens, nonwoven laminates, and film/nonwoven laminates. The particular structure and composition of the liquid impermeable backsheet layer may be selected from various known films and/or fabrics with the particular material being selected as appropriate to provide the desired level of liquid barrier, strength, abrasion resistance, tactile properties, aesthetics (such as texture and printability) and so forth. Suitable backsheet layer materials include, but are not limited to, those described in U.S. Pat. No. 4,376,799 to Tusim et al., U.S. Pat. No. 4,578,069 to Whitehead et al., U.S. Pat. No. 5,695,849 to Shawver et al, U.S. Pat. No. 6,075,179 et al. to McCormack et al., and U.S. Pat. No. 6,376,095 to Cheung et al., each of which is hereby incorporated by reference thereto in its entirety, to the extent not inconsistent with this disclosure. The liquid impermeable backsheet layer 17 may be breathable or nonbreathable, as may be desired. In one embodiment, the liquid impermeable backsheet layer 17 is a breathable polyolefinic film having a basis weight of between about 18 and 40 gsm, alternatively between about 20 and 30 gsm, such as of a polyethylene film.

As noted, the absorbent articles of the disclosure may include other additional features as are generally known in the art. Such features may include wing or tab-like features 15, which are desirably extensions of the liquid permeable topsheet layer 16 and liquid impermeable backsheet layer 17 of the base-structure 29 that extend out from the opposing longitudinal side edges of the absorbent article 10. Such wings 15 may also be nonintegral in construction, either being attached only to the liquid permeable topsheet layer 16 or the liquid impermeable backsheet layer 17.

Pillow-like absorbent features may also be placed along the longitudinal side edges of the absorbent article base structure in order to provide for enhanced fit and/or lateral barrier-like features for further leakage prevention along the side edges. Such are illustrated for instance in United States Patent Publication US2014/0358106 to Tan et al. which is hereby incorporated by reference thereto in its entirety, to the extent that it is not inconsistent with this disclosure. Apertured, fluid transfer or intake layers may also be utilized in connection with absorbent articles having flat-back protection features. Such apertured layers may define relatively large annular openings in the central body exudate deposition region, through which body exudate may directly pass from the fluid permeable topsheet layer to the absorbent layer. Examples of such layers and structure may be found in U.S. Pat. No. 5,810,798 to Finch et al., and United States Patent Publications 2001/0027305 to Raidel et al., and 2012/0277711 to Kim et al., each of which are hereby incorporated by reference thereto in its entirety, to the extent that they are not inconsistent with this disclosure.

The absorbent articles 10 may further be individually wrapped in a pouch, such as those which are commonly known in the art. In such an instance, such absorbent article 10 may be releasably fastened to the inside surface of such pouch for ease of article handling and eventual disposal (not shown). Finally, the absorbent article 10 of the invention may include visual cues, such as coloration, in order to highlight the presence of the flat-back protection feature 30. For example, the flat-back protection feature 30 may be colored differently from the base-structure. Regions of the base-structure lateral to the flat-back protection feature, or adjacent the fastened regions 31, 32 of the feature may likewise be colored differently than the feature so as to highlight the feature. Such visual cues can assist in communicating the functionality of the flat-back protection feature 30, and the placement of the absorbent article 10 such that the flat-back protection feature 30 is positioned in an appropriate location adjacent the wearer's anatomy.

Therefore, an absorbent article having a flat-back, protection feature in accordance with the disclosure provides a comfortable structure with which to direct body exudate to the absorbent layers of an absorbent article and avoid leakage while the wearer is in a number of reclining positions. Such flat feature fits the flat portion of a wearer's intergluteal cleft with reduced possibility of irritation, since it does not include a three-dimension protuberance which extends to an apex along sensitive portions of a wearer's anatomy. By avoiding the inclusion of absorbent materials in the flat-back protection feature, the possibility of a continuous wetness sensation is also reduced. Strategic use of embossment features may provide for ease of manufacturing of the absorbent article with flat-back protection feature, as well as strengthening the feature so as to reduce the possibility of it rupturing during use. Furthermore, placement of longitudinally directed, but spaced-apart embossment features on the absorbent article may assist in the folding of the article prior to use.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent article for capturing body exudate while a wearer of said article is in a supine, prone, or fetal position, and including longitudinal, central longitudinal, transverse, and depth axis, such absorbent article comprising:
    a base structure for retaining body exudate, said base structure including a front region, a middle region, and a back region, said base structure comprising a liquid permeable topsheet layer, a liquid impermeable backsheet layer, and an absorbent layer sandwiched and sealed between said topsheet layer and said backsheet layer,
    a flat-back protection feature positioned along the central longitudinal axis, that is capable of separating in part from the topsheet layer of the base structure in the back region, said flat-back protection feature including two longitudinally directed side edges and further including a first fastening region in which said flat-back protection feature is attached to the topsheet layer in the middle region, a second fastening region in which said flat-back protection feature is attached to the topsheet layer in the back region, and an elevated portion having an unattached length, said unattached length extending continuously between said first fastening region to said second fastening region, and said unattached length being capable of separating from said base structure along the absorbent article depth direction such that a spatial gap is formed between said flat-back protection feature and the base structure along the unattached length, said flat-back protection feature being relatively planar in that it does not include any transverse axis bend that extends uniformly along the elevated portion on the longitudinal axis between the first and second fastening regions, wherein the flat-back protection feature includes at least two different transverse axis widths along the longitudinal axis wherein a wider width of said differing widths is located at the back region, and said flat-back protection feature being formed from sheet material which is capable of carrying body exudate to the middle region and does not include any absorbent materials, and which flat-back protection feature includes a portion along its length which can both lie flat against the intergluteal cleft region of a wearer and which is also capable of separation from said base structure;
    embossment features which extend on the base structure along a longitudinal axis, and which are symmetrically placed laterally beyond the longitudinal side edges of the flat-back protection feature, and on each side of the central longitudinal axis, said embossment features each including a spatial gap along the longitudinal direction with said spatial gap being positioned adjacent the elevated portion,
    and further, wherein any of embossment features cross the central longitudinal axis in locations on said absorbent article in which said flat-back protection feature is not present.

2. The absorbent article of claim 1, wherein said absorbent article includes additional embossing features located in at least one of the first and second fastening regions.

3. The absorbent article of claim 2, wherein said additional embossing features are positioned, on or adjacent to the longitudinal ends of said flat-back protection feature.

4. The absorbent article of claim 1, wherein said flat-back protection feature includes the same transverse axis width along the entire longitudinal axis.

5. The absorbent article of claim 1, wherein said wider width flares outward towards said back end.

6. The absorbent article of claim 2, wherein said additional embossment features include a spatial gap between them.

7. The absorbent article of claim 6, wherein said spatial gap is along the transverse axis.

8. The absorbent article of claim 6, wherein said spatial gap is along the longitudinal axis.

9. The absorbent article of claim 2, wherein said flat-back protection feature includes an elastic material and said additional embossment features are positioned at least partially over said elastic material.

10. The absorbent article of claim 9, wherein said elastic material comprises elastic strands.

11. The absorbent article of claim 9, wherein said embossment features that are lateral to the flat-back protection feature include outwardly flared portions.

12. The absorbent article of claim 1, wherein the absorbent article includes fold lines positioned within the spatial gaps of the embossment features.

13. The absorbent article of claim 1, wherein the flat-back protection feature includes hydrophobic materials.

14. The absorbent article of claim 1, wherein the flat-back protection feature includes only hydrophobic materials.

15. The absorbent article of claim 10, wherein the elastic material is an elastic laminate, including at least one nonwoven layer.

\* \* \* \* \*